United States Patent [19]

Harnden et al.

[11] Patent Number: 5,356,886
[45] Date of Patent: Oct. 18, 1994

[54] ANTIVIRAL PHOSPHONO-ALKEN DERIVATIVES OF PURINES

[75] Inventors: Michael R. Harnden; Martin J. Parratt, both of Epsom, England

[73] Assignee: Beecham Group p.l.c., Middlesex, England

[21] Appl. No.: 965,260

[22] PCT Filed: Jul. 15, 1991

[86] PCT No.: PCT/GB91/01171

§ 371 Date: Jan. 19, 1993

§ 102(e) Date: Jan. 19, 1993

[87] PCT Pub. No.: WO92/01698

PCT Pub. Date: Feb. 6, 1992

[30] Foreign Application Priority Data

Jul. 19, 1990 [GB] United Kingdom ............ 9015865.0
May 18, 1991 [GB] United Kingdom ............ 9110774.8

[51] Int. Cl.$^5$ .................. A61K 31/675; C07F 9/6561
[52] U.S. Cl. ........................ 514/81; 544/244; 549/221; 556/405; 556/482; 558/177
[58] Field of Search ............................ 544/244; 514/81

[56] References Cited

U.S. PATENT DOCUMENTS 4,910,307  3/1990  Wyatt ................. 544/244
5,055,458 10/1991  Bailey et al. ......... 544/244

FOREIGN PATENT DOCUMENTS 173624  3/1986  European Pat. Off. .
0343133 11/1989  European Pat. Off. .

OTHER PUBLICATIONS

Collection of Czechoslovak Chm. Commun., vol. 53, No. 11B, Nov. 1988, I. Rosenberg et al., pp. 2753-2777.

Primary Examiner—Emily Bernhardt
Attorney, Agent, or Firm—Yuriy P. Stercho; Stuart R. Suter; Edward T. Lentz

[57] ABSTRACT

The present invention provides antiviral compounds of Formula (I), and pharmaceutically acceptable salts thereof:

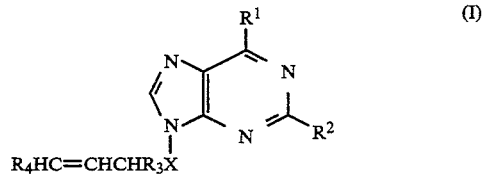

wherein
X is —CH$_2$O or —CH$_2$;
R$_1$ is hydroxy or amino;
R$_2$ is hydrogen or amino;
R$_3$ is hydrogen, hydroxymethyl or acyloxymethyl, wherein the acyl group of said acyloxymethyl is selected from the group consisting of C$_{1-7}$ alkanoyl and benzoyl optionally substituted in the phenyl ring by one, two or three substituents selected from the group consisting of fluoro, chloro, bromo, C$_{1-4}$ alkyl and C$_{1-4}$ alkoxy, wherein the alkyl moiety of said C$_{1-4}$ alkyl and C$_{1-4}$alkoxy substituents is selected from the group consisting of methyl, ethyl, n- and iso-propyl, n-, sec-, iso- and tert-butyl,
R$_4$ is a group of formula:

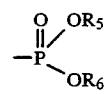

wherein
R$_5$ and R$_6$ are independent selected from hydrogen, C$_{1-6}$ alkyl and phenyl optionally substituted by one, two or three substituents selected from the group consisting of fluoro, chloro, bromo, C$_{1-4}$ alkyl and C$_{1-4}$ alkoxy, wherein the alkyl moiety of said C$_{1-4}$ alkyl and C$_{1-4}$ alkoxy substituents is selected from the group consisting of methyl, ethyl, n- and iso-propyl, n-, sec-, iso- and tert-butyl.

8 Claims, No Drawings

ANTIVIRAL PHOSPHONO-ALKEN DERIVATIVES OF PURINES

The present invention relates to compounds having antiviral activity, to processes for their preparation and to their use as pharmaceuticals.

Coll. Czech. Chem. Commun., 1988, 53, 2753 (Rosenberg et. al.) describes phosphonylalkyl derivatives of adenine.

EP-A-343133 (Medivir Aktiebolag) discloses a group of phosphonylalkyl purine derivatives which are described as having antiviral activity.

EP-A-404296 (Beecham group p.l.c.), published 27.12.90, describes a group of phosphonylalkoxy purine derivatives having antiviral activity.

A novel, structurally distinct class of compounds has now been discovered, these compounds being phosphonylalkenyl or phosphonylalkenyloxy derivatives of purine, and also having antiviral activity.

Accordingly, the present invention provides a compound of formula (I), or a pharmaceutically acceptable salt thereof:

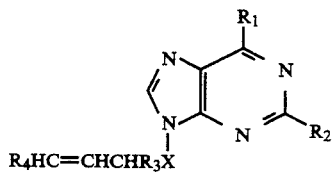

(I)

wherein

X is —$CH_2O$ or —$CH_2$;
$R_1$ is hydroxy or amino;
$R_2$ is hydrogen or amino;
$R_3$ is hydrogen, hydroxymethyl or acyloxymethyl; and
$R_4$ is a group of formula:

wherein
$R_5$ and $R_6$ are independently selected from hydrogen, $C_{1-6}$ alkyl and optionally substituted phenyl.

When $R_1$ is hydroxy and $R_2$ is amino, the compound of formula (I) is a guanine derivative;

When $R_1$ is amino and $R_2$ is hydrogen, the compound of formula (I) is an adenine derivative;

When $R_1$ is hydroxy and $R_2$ is hydrogen, the compound of formula (I) is a hypoxanthine derivative; and When $R_1$ and $R_2$ are both amino groups, the compound of formula (I) is a 2,6-diaminopurine derivative.

Often, the compound of formula (I) is a guanine or adenine derivative.

Suitable examples of the acyl group in $R_3$ when acyloxymethyl, include carboxylic acyl, Such as $C_{1-7}$ alkanoyl and benzoyl optionally substituted in the phenyl ring as defined below for $R_5/R_6$. Preferred acyl groups include acetyl, propionyl, butyryl, heptanoyl and hexanoyl.

Suitable examples of $R_5$ and $R_6$ include hydrogen, methyl, ethyl, n- and iso-propyl, n-, sec-, iso- and tert-butyl, and phenyl optionally substituted by one, two or three groups or atoms selected from halogen, such as fluoro, chloro, bromo, and $C_{1-4}$ alkyl or $C_{1-4}$ alkoxy wherein the alkyl moiety is selected from those listed for $R_5/R_6$ above.

Examples of pharmaceutically acceptable salts of the compound of formula (I) are acid addition salts formed with a pharmaceutically acceptable acid such as hydrochloric acid, orthophosphoric acid and sulphuric acid. Pharmaceutically acceptable salts also include those formed with organic bases, preferably with amines, such as ethanolamines or diamines; and alkali metals, such as sodium and potassium.

As the compound of formula (I) contains a phosphonate group, suitable salts include metal salts, such as alkali metal salts, for example sodium or potassium, alkaline earth metal salts such as calcium or magnesium and ammonium or substituted ammonium salts, for example those with lower alkylamines such as triethylamine, hydroxy-lower alkylamines such as 2-hydroxyethylamine, bis-(2-hydroxyethyl)amine or tris-(2-hydroxyethyl)amine.

It will be appreciated that some of the compounds of formula (I), especially those wherein $R_3$ is other than hydrogen, have an asymmetric centre, and therefore are capable of existing in more than one stereoisomeric form. The invention extends to each of these forms individually and to mixtures thereof, including racemates. The isomers may be separated conventionally by chromatographic methods or using a resolving agent. Alternatively, the individual isomers may be prepared by asymmetric synthesis using chiral intermediates.

It will also be appreciated that, since the compounds of formula (I) contain a $R_4HC=CH$ moiety, they are capable of existing in E and Z (trans and cis) forms. The invention extends to each of these forms and to mixtures thereof.

The compounds of formula (I) including their alkali metal salts may form solvates such as hydrates and these are included wherever a compound of formula (I) or a salt thereof is herein referred to.

It will be appreciated that, when $R_1$ is hydroxy in formula (I) the compound exists in the predominant tautomeric form of structure (IA):

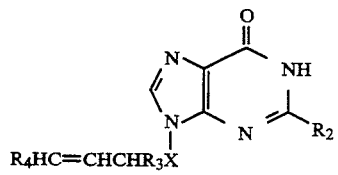

(IA)

The invention also provides a process for the preparation of a compound of formula (I), or a pharmaceutically acceptable salt thereof, which process comprises condensing a compound of formula (II):

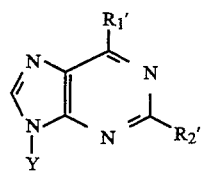

(II)

with a side chain intermediate of formula (III):

$R_4'HC=CHCHR_3'CH_2OH$ (III)

wherein, when X is —CH₂O in formula (I), Y is OH and, when X is —CH₂, Y is H; $R_1'$, $R_2'$, $R_3'$ and $R_4'$ are $R_1$, $R_2$, $R_3$ and $R_4$ respectively, or groups or atoms convertible thereto; and thereafter, when desired or necessary, converting $R_1'$, $R_2'$, $R_3'$ and/or $R_4'$ when other than $R_1$, $R_2$, $R_3$ and/or $R_4$ to $R_1$, $R_2$, $R_3$ and/or $R_4$ respectively, and/or converting $R_1'$, $R_2'$, $R_3'$ and/or $R_4'$ when $R_1$, $R_2$, $R_3$ and/or $R_4$, to other $R_1$, $R_2$, $R_3$ and/or $R_4$,and/or forming a pharmaceutically acceptable salt thereof.

The reaction takes place in the presence of a dehydrating catalyst, such as diethyl azodicarboxylate in the presence of triphenylphosphine.

Examples of conversions of variable groups are as follows:

$R_1'$—$R_1$ a) An $R_1$ hydroxy group may be converted to $R_1'$ is chloro, by chlorination using a reagent such as phosphorus oxychloride, preferably in the presence of tetraethylammonium chloride and dimethylaniline (as acid acceptor) in CH₃CN at reflux temperatures, according to the method described by M. J. Robins and B. Ozanski, Can. J. Chem, 59, 2601 (1981).

b) An $R_1'$ chloro group may be converted to $R_1$ is hydroxy by hydrolysis using aqueous mineral acid, such as hydrochloric acid, or more preferably, using an organic acid, such as formic acid at elevated temperature, suitably 70°–150° C., preferably around 100° C.

c) An $R_1'$ chloro group may be converted to $R_1$ is amino by treatment with ammonia in a lower alkanol, such as ethanol or methanol in an autoclave at 100° C. for a period of about 7 hours, or alternatively, by treatment with sodium azide in dimethylformamide (forming an $R_1$ is $N_3$ intermediate), followed by reduction with ammonium formate/palladium on charcoal, in methanol or with triphenylphosphine in water as described by Vaulter et al., Tet. Letts. 24(8) 763–764(1983).

d) An $R_1'$ alkoxy group, such as methoxy, may be converted to $R_1$ hydroxy by the methods of D. R. Haines, J. Med. Chem. 1987, 30, 943 and K. K. Ogilvie and H. R. Hanna, Can. J. Chem. 1984, 62, 2702, or using trimethylsilyl bromide, as described in Example 1b) hereinafter.

e) An $R_1'$ protected amino group, such as tritylamino, may be converted to amino, by treatment with aqueous acetic acid, preferably 80% acetic acid at elevated temperature, around 80° C. $R_1'$ may also be phthalimido, which may be converted to amino by treatment with methyl hydrazine or hydrazine in an inert solvent, such as dichloromethane, at ambient temperature.

$R_2'$—$R_2$ a) $R_2'$ may be protected amino, such as formylamino, which may be converted to $R_2$ is amino by hydrolysis; or $R_2'$ may be di-t-butyloxycarbonylamino.

$R_3'$—$R_3$ a) Hydroxymethyl may be converted to acyloxy or acyloxymethyl respectively by conventional acylation procedures.

b) Protected hydroxymethyl may be converted to hydroxymethyl by conventional deprotection methods.

Suitable examples of protecting groups and their removal, are as described in EP-A-242482. A particularly suitable protecting group is the t-butyldiphenylsilyl group removable by conventional methods.

$R_4'$—$R_4$

When $R_5$ and $R_6$ in $R_4$ are other than hydrogen, they may be converted to $R_5$ and $R_6$ are hydrogen, using a deesterifying reagent, such as trimethylsilyl bromide in an aprotic solvent such as dichloromethane or dimethylformamide at ambient temperature, as described by C. E. McKenna et. al., J.C.S., Chem. Comm., 1979, 739.

Selective conversion of one of $R_5$ and $R_6$ to hydrogen, may be achieved by treatment with hydroxide ion, as described by Rabinowitz JACS, 1960, 82, 4564.

It will be appreciated that the above conversions may take place in any desired or necessary order, having regard to the final desired compound of formula (I).

Compounds of the formula (II) wherein Y is OH are prepared as described in EP-A-313289 and EP-A-319228 (both Beecham Group p.l.c.), from compounds of formula (IV) wherein the 5-amino group is formylated:

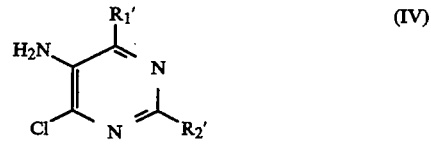

(IV)

by reaction with R₇ONH₂ wherein R₇ is a protecting group, to give a compound of formula (V):

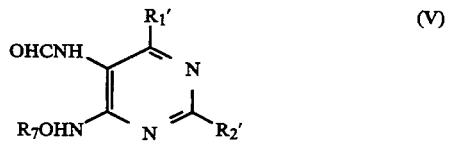

(V)

which may be cyclised with diethoxymethyl acetate, to give a compound of formula (II) wherein the OH group is protected. Suitable values for R₇ include benzyl, removable by hydrogenation, and the tetrahydropyran-2-yl group removable by treatment with 80% acetic acid, at ambient temperature.

Compounds of the formula (II) wherein Y is H are generally known, for example, 2-amino-6-chloropurine may be prepared as described in EP-A-203685 (Beecham Group p.l.c.).

Intermediates of the formula (III) (E-isomers) may be prepared as follows:

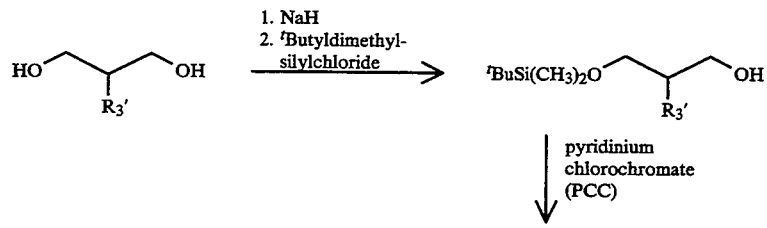

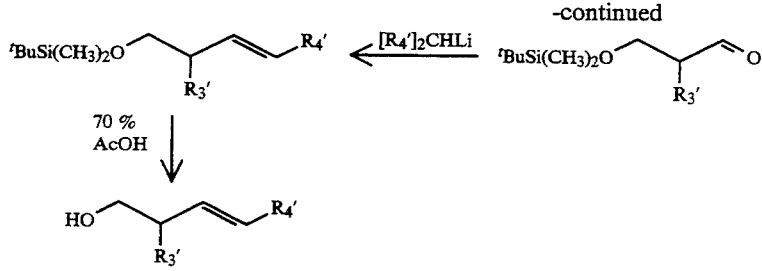

-continued $R_4'$ in the above is a value of $R_4$, usually wherein $R_5$ and $R_6$ are other than hydrogen. $R_3'$ is hydrogen or protected hydroxymethyl.

Intermediated of the formula (III) (z-isomers) may be prepared as described in Description 2 hereinafter.

When $R_3$ is hydroxymethyl, appropriate selective protection on one of the hydroxy groups in the side chain intermediate of formula (III) is required, e.g. using acetate; or the 'butyl dimethylsilyl protecting group may be replaced by the isopropylidine joined together with $R_3'$.

Intermediates of the formula (III) wherein $R_4'$ is $R_4$ as defined in formula (I), are novel and form an aspect of the invention.

Pharmaceutically acceptable salts may be prepared in conventional manner, for example, in the case of acid addition salts, by reaction with the appropriate organic or inorganic acid.

It will be appreciated that the invention provides a process for the preparation of a compound of formula (I) wherein $R_3$ is hydroxymethyl which process comprises the deprotection of a corresponding compound of formula (I) wherein $R_3$ is protected hydroxymethyl.

Preferred methods for deprotection, as hereinbefore described, include removal of the acetyl group.

The invention also provides a process for the preparation of a compound of formula (I) wherein $R_5$ and $R_6$ are both hydrogen, which process comprises the deesterification of a corresponding compound of formula (I) wherein $R_5$ and $R_6$ are the same alkyl or optionally substituted phenyl group.

It will be appreciated that, in some circumstances, it may be possible to prepare the compounds of formula (I) by methods analogous to those generally described in EP-A-404296 (Beecham Group p.l.c.) having regard to the unsaturated side chain and the need for protection of the unsaturated moiety and/or modification of reaction conditions.

The compounds of the invention are of potential use in the treatment of infections caused by DNA viruses. Examples of DNA viruses include herpesviruses such as herpes simplex types 1 and 2, varicella-zoster virus, Epstein-Barr virus and cytomegalovirus.

Compounds of the invention may be formulated for use in a pharmaceutical composition. Accordingly, in a further aspect of the invention, there is provided a pharmaceutical composition which comprises a compound Of formula (I) or pharmaceutically acceptable salt thereof together with a pharmaceutically acceptable carrier or excipient.

A composition which may be administered by the oral route to humans may be compounded in the form of a syrup, tablet or capsule. When the composition is in the form of a tablet, any pharmaceutical carrier suitable for formulating such solid compositions may be used, for example magnesium stearate, starch, lactose, glucose, rice, flour and chalk. The composition may also be in the form of an ingestible capsule, for example of gelatin, to contain the compound, or in the form of a syrup, a solution or a suspension. Suitable liquid pharmaceutical carriers include ethyl alcohol, glycerine, saline and water to which flavouring or colouring agents may be added to form syrups. The compounds may also be presented with a sterile liquid carrier for injection.

The composition may also be formulated for topical application to the skin or eyes.

For topical application to the skin, the composition may be in the form of a cream, lotion or ointment. These formulations may be conventional formulations well known in the art, for example, as described in standard books of pharmaceutics and cosmetics, such as Harry's Cosmeticology published by Leonard Hill Books and the British Pharmacopaeia.

The composition for application to the eyes may be a conventional eye-drop composition well known in the art, or an ointment composition.

Preferably, the composition of this invention is in unit dosage form or in some other form that may be administered in a single dose. A suitable dosage unit might contain from 50 mg to 1 g of active ingredient, for example 100 to 500 mg.

Such doses may be administered 1 to 4 times a day or more usually 2 or 3 times a day. The effective dose of compound will in general be in the range of from 1.0 to 20 mg/kg of body weight per day or more usually 2.0 to 10 mg/kg per day.

No unacceptable toxicological effects are indicated at the above described dosage levels.

The invention also provides a method of treating viral infections in a human or non-human animal, which comprises administering to the animal an effective, non-toxic amount of a compound of formula (I) or a pharmaceutically acceptable salt thereof.

The invention also provides a compound of formula (I) or a pharmaceutically acceptable salt thereof for use as an active therapeutic substance, in particular for the treatment of viral infections.

The compounds of the invention are also believed to exhibit a synergistic antiherpesvirus effect in conjunction with interferons; and combination products comprising these two components for sequential or concomitant administration, by the same or different routes, are therefore within the ambit of the present invention.

The following examples illustrate the invention; the following descriptions illustrate the preparation of intermediates.

DESCRIPTION 1

Intermediates for Examples 1 to 8
a) 3-(t-Butyldimethylsiyloxy)propan-1-ol

To a suspension of sodium hydride (6.29 g, 262 mmol) in dry tetrahydrofuran (400 ml) was added 1,3-propanediol (20.0 g, 262 mmol) over 5 min and the mixture was stirred at room temperature under dry nitrogen for 1.5 hr. t-Butyldimethylsilyl chloride (39.5 g, 262 mmol) was added portionwise and the mixture was stirred at room temperature for 1.5 hr. Saturated sodium chloride solution (300 ml) then ether (500 ml) were added. The organic portion was dried (magnesium sulphate), filtered and the solvent removed. The residue was purified by column chromatography on silica gel eluting with ether-hexane (1:2, 3:2) to afford 3-(t-butyldimethylsilyloxy)propan-1-ol as a colourless liquid (41.2 g, 83%); $\delta_H$(CDCl$_3$) 0.10 (6H, s, CH$_3$), 0.93 (9H, s, C(CH$_3$)$_3$), 1.80 (2H, qu, J 6 Hz, CH$_2$), 2.37 (1H, br.s, OH), 3.87 (4H, m, CH$_2$O ).

b) 3-(t-Butyldimethylsilyloxy)propanal

To a suspension of pyridinium chlorochromate (8.50 g, 39.4 mmol) in dichloromethane (53 ml), stirred at room temperature under dry nitrogen, was added 3-(t-butyldimethylsilyloxy)propan-1-ol (5.00 g, 26.3 mmol). After 1.5 hr, dry ether (50 ml) was added and the supernatant liquid decanted from a black gum. The residual gum was washed with ether (3×50 ml) and the combined organic portions passed through a column of Florisil. The resulting brown solution was evaporated then the residue taken up in dichloromethane and passed through fresh Florisil to give a yellow solution from which the solvent was removed to leave a brown liquid (2.75 g). This material was shown by $^1$Hnmr analysis to be approximately 40% pure and was used without further purification; $\delta_H$(CDCl$_3$) 0.10 (6H, s, CH$_3$), 0.93 (9H, s, C(CH$_3$)$_3$), 0.63 (2H, dt, J 2 HZ and 6 Hz respectively, CH$_2$), 4.03 (2H, t, J 6 Hz, CH$_2$O ), 9.97 (1H, d, J 2 Hz, CHO).

c) Diisopropyl (E)-4-(t-butyldimethylsilyloxy) but-1-enylphosphonate

To a solution of tetraisopropyl methylenebisphosphonate (2.50 g, 7.26 mmol) in n-heptane (50 ml) was added n-butyllithium (2.70 ml of 2.7M solution in n-hexanes; 7.29 mmol) and the mixture stirred at room temperature under dry nitrogen for 15 min. To the solution was added crude 3-(t-butyldimethylsilyloxy) propanal (approx. 5.85 mmol) and the mixture heated under reflux for 0.5 hr then stirred at room temperature for 64 hr. The mixture was filtered then the solvent removed. The residue was purified by column chromatography on silica gel eluting with dichloromethane-ethyl acetate (9:1, 4:1) to afford diisopropyl (E)-4-(t-butyldimethylsilyloxy)but-1-enylphosphonate as a colourless oil (1.10 g, 43%); $\nu_{max}$ (film) 2940, 1625, 1460, 1380, 1250, 1105, 980 and 830 cm$^{-1}$; $\delta_H$(CDCl$_3$) 0.03 (6H, s, SiCH$_3$), 0.90 (9H, s, C(CH$_3$)$_3$), 1.32 (12H, dd, J 3 Hz and 6 Hz, CH(CH$_3$)$_2$), 2.43 (2H, m, CH$_2$), 3.72 (2H, t, J 7 Hz, CH$_2$O ), 4.65 (2H, m, CH(CH$_3$)$_2$), 5.72 (1H, dd, J 17 Hz and 20 Hz, PCH=CH), 6.75 (1H, ddt, J 7 Hz, 17 Hz and 20 Hz, PCH=CH); FABMS(thioglycerol) 351 (MH+) (Found: C, 54.76; H, 10.05%. C$_{16}$H$_{35}$O$_4$PSI requires C, 54.84; H, 10.07%).

d) Diisopropyl (E)-4-hydroxybut-1-enylphosphonate

A solution of diisopropyl (E)-4-(t-butyldimethylsilyloxy)but-1-enylphosphonate (0.84 g, 2.40 mmol) in acetic acid-water (2:1) (10 ml) was stirred at 70° C. for 2 hr. The solvent was removed and the residue purified by column chromatography on silica gel eluting with acetone-hexane (1:1) to give diisopropyl (E)-4-hydroxybut-1-enylphosphonate as a gum (0.43 g, 76%); $\nu_{max}$ (film) 3380, 2970, 1625, 1460, 1380, 1370, 1220 and 980 cm$^{-1}$; $\delta_H$(CDCl$_3$) 1.32 (12H, dd, J 9 Hz and 6 Hz, CH(CH$_3$)$_2$), 1.85 (1H, br.s, OH), 2.50 (2H, m, CH$_2$), 3.76 (2H, t, J 6 Hz, CH$_2$O ), 4.69 (2H, m, CH(CH$_3$)$_2$), 5.80 (1H, dd, J 16 Hz and 18 Hz, PCH=CH) 6.75 (1H, ddt, J 7 Hz, 17 Hz and 22 Hz, PCH=CH); CIMS (isobutane) 237 (MH+).

DESCRIPTION 2

Intermediate for Examples 9, 10 and 11 a) Diethyl (Z)-4-(t-butyldimethylsilyloxy)but-1-enylphosphonate

To a solution of n-butyllithium in hexane (38.9 ml, 2.7M, 105 mmol) stirred at −20° C. under dry nitrogen was added a solution of diisopropylamine (11.5 g, 114 mmol) in dry THF (70 ml). The solution was cooled to −70° C. before a solution of diethyl methylphosphonate (7.6 g, 50 mmol) in dry THF (10 ml) was added dropwise. A solution of chlorotrimethylsilane (5.8 g, 53 mmol) in dry THF (15 ml) was then added dropwise, maintaining the internal temperature below −60° C. The resulting solution was stirred at −70° C. for 15 min. then warmed to −20° C. before a solution of 3-(t-butyldimethylsilyloxy)propanal (approx. 46 mmol) in dry THF (10 ml) was added dropwise. The solution was then stirred at room temperature for 1.5 hr. The reaction mixture was neutralized by addition of 2M hydrochloric acid and extracted with ether (250 ml). The organic phase was dried (magnesium sulphate), filtered and the solvent removed. The residual oil was purified by column chromatography on silica gel eluting with hexane-acetone (5:1, 3:1) to afford diethyl (Z)-4-(t-butyldimethylsilyloxy)but-1-enylphosphonate as a colourless liquid (1.5 g, 9%); $\nu_{max}$ (film) 2940, 1625, 1390, 1245, 1095, 1055, 1030 and 950 cm$^{-1}$; $\delta_H$(CDCl$_3$) 0.05 (6H, s, SiCH$_3$), 0.87 (9H, s, C(CH$_3$)$_3$), 1.30 (6H, t, J 7 Hz, CH$_3$), 2.83 (2H, m, CH$_2$), 3.73 (2H, t, J 7 Hz, CH$_2$OSi), 4.10 (4H, qu, J 7 Hz, CH$_2$O ), 5.70 (1H, dd, J 14 Hz and 20 Hz, PCH=CH), 6.70 (1H, ddt, J 7 Hz, 14 Hz and 54 Hz, PCH=CH) (Found: MH+ 323.1808. C$_{14}$ b) Diethyl (Z)-4-hydroxybut-1-enylphosphonate A solution of diethyl (Z)-4-(t-butyldimethylsilyloxy)-but-1-enylphosphonate (1.32 g, 4.09 mmol) in acetic acid-water (2:1) (35 ml) was stirred at room temperature for 2 hr. The solvent was removed and the residue was purified by column chromatography on silica gel eluting with dichloromethane-methanol (19:1) to give diethyl (Z)-4-hydroxybut-1-enylphosphonate as a colourless liquid (0.5 g, 59%); $\nu_{max}$ (film) 3380, 2980, 1720, 1620, 1390, 1230 and 1020 cm$^{-1}$; $\delta_H$(CDCl$_3$) 1.33 (6H, t, J 7 Hz, CH$_3$), 2.70 (2H, m, CH$_2$), 3.15 (1H, s, OH), 3.73 (2H, t, J 7 Hz, CH$_2$O ), 4.00 (4H, qu, J 7 Hz, CH$_3$CH$_2$), 5.70 (1H, dd, J 14 Hz and 20 Hz, PCH=CH), 6.60 (1H, ddt, J 7 Hz, 14 Hz and 54 Hz, PCH=CH) (Found: MH+ 209.0942. C$_8$H$_{17}$O$_4$P requires MH+ 209.0943).

DESCRIPTION 3

Intermediates for Examples 12-18 a) Diisopropyl (E)-2-(1,3-dioxan-5-yl)ethenylphosphonate

A solution of 2-(1,3-dioxan-5-yl)ethanol (2 g, 14 mmol) in dichloromethane (5 ml) was added dropwise to pyridinium chlorochromate (4.4 g, 20 mmol) in dichloromethane (30 ml). The mixture was stirred at room temperature for 2 h, then treated with ether (30 ml). After stirring for a further 10 min, at room temperature, the mixture was filtered through silica, the residue extracted with ether (50 ml), filtered and the combined filtrates evaporated in vacuo to give an oil (0.75 g) which was shown by 90 MHz n.m.r. to contain 60% aldehyde (23%).

A solution of tetraisopropyl methylenebisphosphonate (1 g, 3.1 mmol) in heptane (25 ml) was treated with 2.7M n-butyllithium in hexane (1.1 ml, 3.1 mmol). After stirring at room temperature for 15 min, the aldehyde obtained above (0.75 g, 60% pure, 3.1 mmol), suspended in heptane (5 ml) was added. After stirring at room temperature for 15 min, the solvent was removed and the residue chromatographed on silica gel, eluting with acetone-hexane (1:4) to give diisopropyl (E)-2-(1,3-dioxan-5-yl)ethenylphosphonate as an oil (0.88 g, 98%); $v_{max}$(KBr) 3386, 2979, 2938, 2870, 1740, 1627, 1470,and 1455 cm$^{-1}$; $\delta_H$(CDCl$_3$) 1.30(6H, d, J 6 Hz, 2×CH$_3$CH), 1.33 (6H, d, J 6 Hz, 2×CH$_3$CH), 1.42 (3H, s, CH$_3$), 1.44 (3H, s, CH$_3$), 2.65 (1H, m, CH), 3.85 (4H, m, 2×CH$_2$), 4.55 [2H, m, 2×CH(CH$_3$)$_2$], 5.79 (1H, ddd, J 1, 17 and 19 Hz, PCH=CH), 6.60 (1H, ddd, J 7, 17 and 22 Hz, PCH=CH) (Found: C, 55.03; H, 8.94%. C$_{14}$H$_{27}$O$_5$P requires C, 54.89; H, 8.88%).

b) Diisopropyl (E)-4(hydroxy-3-hydroxymethylbut-1-enylphosphonate

A solution of diisopropyl (E)-2-(1,3-dioxan-5-yl)ethylphosphonate (0.73 g, 2.4 mmol) in 3% methanolic HCl (10 ml) was stirred at room temperature for 1.5 h. The solvent was removed in vacuo and the residue chromatographed on silica gel eluting with ethyl acetate, increasing polarity to ethyl acetate-methanol (20:1) to give diisopropyl (E)-4-hydroxy-3-hydroxymethyl-but-1-enylphosphonate as an oil (0.4 g, 63%): $v_{max}$(film) 3391, 2979, 2933, 2877, 1738, 1630, 1467,and 1454 cm$^{-1}$; $\delta_H$(CDCl$_3$) 1.32 (6H, d, J 6 Hz, 2×CH$_3$CH), 1.32 (6H, d, J 6 Hz, 2×CH$_3$CH), 2.61 (1H, m, CH), 3.40 (2H, br.s, D$_2$O exchangeable OH's), 3.80 (4H, m, 2×CH$_2$OH), 4.65 [2H, m, 2×CH(CH$_3$)$_2$], 5.82 (1H, ddd, J 1, 17 and 20 Hz, PCH=CH), 6.71 (1H, ddd, J 7, 17 and 23 Hz, PCH=CH) (Found: C, 49.52; H, 9.04. C$_{11}$H$_{23}$O$_5$P requires C, 49.62; H, 8.71%).

c) Diisopropyl (E)-3-acetoxymethyl-4-hydroxybut-1-enylphosphonate

A solution of diisopropyl (E)-4-hydroxy-3-hydroxymethylbut-1-enylphosphonate (5 g, 19 mmol), trimethyl orthoacetate (7 ml, 56 mmol) and p-toluenesulphonic acid (0.36 g, 1.9 mmol) in anhydrous THF (50 ml) was stirred at room temperature for 1.5 h. The solution was treated with water (5 ml), stirred for a further 30 min, then treated with triethylamine (0.1 ml). The solvent was removed in vacuo and the residue chromatographed on silica, eluting with chloroform-methanol (30:1) to give diisopropyl (E)-3-acetoxymethyl-4-hydroxybut-1-enylphosphonate as an oil (4.94 g, 85%);$v_{max}$ (film) 3382, 2980, 2934, 2877, 2361, 2333, 1741, 1631, 1468,and 1455 cm$^{-1}$; $\delta_H$(CDCl$_3$) 1.30 (6H, d, J 6.3 Hz, 2×CH$_3$CH), 1.34 (6H, d, J 6 Hz, 2×CH$_3$CH) 2.06 (3H, s, CH$_3$CO), 2.40 (1H, br.s, D$_2$O exchangeable OH), 3.68 (2H, m, CH$_2$OH), 424 (2H, m, CH$_2$), 4.64 [2H, m, 2×CH(CH$_3$)$_2$], 5.83 (1H, ddd, J 1, 17 and 19 Hz, PCH=CH), 6.67 (1H, ddd, J 8, 17 and 22 Hz, PCH=CH) (Found: C, 50.15; H, 8.46%; MH+ 309.1466. C$_{13}$H$_{17}$O$_6$P.0.25 H$_2$O requires: C, 49.95; H, 8.22%; MH+ 309.1467).

d) Diisopropyl (E)-3-acetoxymethyl-4-t-butyldiphenylsilyloxybut-1-enylphosphonate To a solution of diisopropyl (E)-3-acetoxymethyl-4-hydroxybut-1-enylphosphonate (3 g, 9.7 mmol ) and imidazole (1.7 g, 25 mmol) in anhydrous THF (60 ml) at 0° C. was added t-butyldiphenylsilylchloride (3.2 ml, 12.7 mmol). After stirring at room temperature for 3 h, the solvent was removed and the residue was partitioned between chloroform (100 ml) and brine (30 ml). The organic phase was dried (MgSo$_4$), evaporated in vacuo and chromatographed on silica gel, eluting with chloroform of increasing polarity to chloroform-methanol (100:1) to give diisopropyl (E)-3-acetoxymethyl-4-t-butyldiphenylsilyloxybut-1-enylphosphonate as an oil (5 g, 94%); $v_{max}$ (film) 3071, 3050, 2977, 2931, 2858, 1743, 1630, 1582, 1472,and 1425 cm$^{-1}$; $\delta_H$ (CDCl$_3$) 1.05 [9H, s, C(CH$_3$)$_3$], 1.26 (3H, d, J 6 Hz, CH$_3$CH), 1.27 (3H, d, J 6 Hz, CH$_3$CH), 1.32 [6H, d, J 6.3 Hz, (CH$_3$)$_2$CH], 1.98 (3H, s, CH$_3$CO), 2.74 (1H, m, CH), 3.72 (2H, m, CH$_2$), 4.22 (2H, m, CH$_2$), 4.65 (2H, m, 2×CH(CH$_3$)$_2$], 5.76 (1H, ddd, J 1, 17 and 18 Hz, PCH=CH), 6.99 (1H, ddd, J 7, 17 and 22 Hz, PCH=CH), 7.3-7.7 (10H, m, 2×C$_6$H$_5$) (Found: C, 63.42; H, 8.22%. C$_{29}$H$_{43}$O$_6$PSi requires C, 63.71; H, 7.93%.).

e) Diisopropyl (E)-3-(t-butyldiphenylsilyloxy)methyl-4-hydroxybut-1-enylphosphonate A solution of diisopropyl (E)-3-acetoxymethyl-4-t-butyldiphenylsilyloxybut-1-enylphosphonate (5 g, 9.2 mmol) in methanol (50 ml) was stirred with potassium carbonate (63 g, 0.45 mmol) for 5 h at room temperature. The solvent was removed in vacuo and the residue was chromatographed on silica gel eluting with chloroform-methanol (100:1) of increasing polarity to (30:1) to give diisopropyl (E)-3-t-butyldiphenylsilyloxymethyl-4-hydroxybut-1-enylphosphonate as an oil (3.4 g, 73%): $v_{max}$ (film) 3381, 3071, 3025, 2940, 2931, 2858, 2360, 2332, 1631, 1585, 1471 and 1428 cm$^{-1}$; $\delta_H$(CDCl$_3$) 1.05 [9H, s, C(CH$_3$)$_3$], 1.25 (3H, d, J 6 Hz, CHCH$_3$), 1.27 (3H, d, J 6.1 Hz, CHCH3), 1.31 [6H, d, J 6 Hz, CH(CH$_3$)$_2$], 2.15 (1H, t, J 5.9 Hz, D$_2$O exchangeable OH), 2.65 (1H, m, CH), 3.80 (4H, m, 2×CH$_2$), 4.65 [2H, m, 2×CH(CH$_3$)$_2$], 5.76 (1H, ddd, J 1, 17 and 19 Hz, PCH=CH), 6.64 (1H, ddd, J 8, 17 and 23 Hz, PCH=CH), 7.4-7.7 (10H, m, 2×C$_6$H$_5$) (Found: C, 63.65; H, 8.16%. M+ 504.2444. C$_{27}$H$_{41}$O$_5$PSi.0.25 H$_2$O requires C, 63.69; H, 8.22%. M+ 504.2461).

EXAMPLES

The following compounds were prepared:

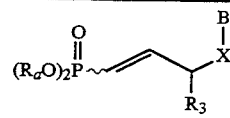

A = adenine
G = guanine
D = 2,6-diaminopurine

| Example No. | B | $R_a$ | $R_3$ | X | Isomer |
|---|---|---|---|---|---|
| 1 | G | H | H | CH$_2$O | E |
| 2 | A | $^i$Pr | H | CH$_2$O | E |
| 3 | A | H | H | CH$_2$O | E |
| 4 | A | $^i$Pr | H | CH$_2$ | E |
| 5 | A | H | H | CH$_2$ | E |
| 6 | G | H | H | CH$_2$ | E |
| 7 | D | $^i$Pr | H | CH$_2$ | E |
| 8 | D | H | H | CH$_2$ | E |
| 9 | A | Et | H | CH$_2$O | Z |
| 10 | A | H | H | CH$_2$O | Z |
| 11 | G | H | H | CH$_2$O | Z |
| 12 | G | $^i$Pr | CH$_2$OH | CH$_2$O | E |
| 13 | G | H | CH$_2$OH | CH$_2$O | E |
| 14 | A | $^i$Pr | CH$_2$OH | CH$_2$O | E |
| 15 | A | H | CH$_2$OH | CH$_2$O | E |
| 16 | A | $^i$Pr | CH$_2$OH | CH$_2$ | E |

-continued

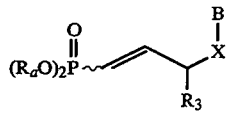

A = adenine
G = guanine
D = 2,6-diaminopurine

| Example No. | B | $R_a$ | $R_3$ | X | Isomer |
|---|---|---|---|---|---|
| 17 | A | H | CH$_2$OH | CH$_2$ | E |
| 18 | G | H | CH$_2$OH | CH$_2$ | E |

EXAMPLE 1

(E)-9-(4-Phosphonobut-3-enyloxy)quanine a) To a mixture of 2-[di-(t-butoxycarbonyl)]amino-9-hydroxy-6-methoxypurine (154 mg, 404 μmol), diisopropyl (E)-4-hydroxybut-1-enylphosphonate (89 mg, 404 μmol) and triphenylphosphine (159 mg, 606 μmol) in dry tetrahydrofuran (4 ml) stirred at 0° C. was added diethyl azodicarboxylate (105 mg, 606 μmol). The mixture was allowed to warm to room temperature and stirred for 2.3 hr. The solvent was removed and the residue was purified by column chromatography on silica gel eluting with ethyl acetate-methanol (20:1) to give (E)-2-[di-(t-butoxycarbonyl)]amino-9-[4-(diisopropoxyphosphoryl)but-3-enyloxy]-6-methoxypurine as a colourless gum (150 mg, 62%); $\lambda_{max}$ (EtOH) 255 (12,300)nm; $v_{max}$ (KBr) 3440, 3220, 2975, 1790, 1600, 1370, 1280 and 1100 cm$^{-1}$; $\delta_H$[(CD$_3$)$_2$SO] 1.22 (12H, dd, J 6 Hz and 7 Hz, CH(CH$_3$)$_2$), 1.40 (18H, S, C(CH$_3$)$_3$), 2.70 (2H, m, CH$_2$), 4.08 (3H, s, CH$_3$O), 4.53 (4H, m, CH$_2$O and CH(CH$_3$)$_2$), 5.98 (1H, dd, J 17 Hz and 19 Hz, PCH=CH), 6.25 (1H, ddt, J 6 Hz, 17 Hz and 22 Hz, PCH=CH), 8.71 (1H, s, 8-H) (Found: M+ 599.2724. C$_{26}$H$_{42}$N$_5$O$_9$P requires M+ 599.2720).

b) To a solution of (E)-2-[di-(t-butoxycarbonyl)]-amino-9-[4-(diisopropoxyphosphoryl)but-3-enyloxy]-6-methoxypurine (106 mg, 177 μmol) in dichloromethane (5 ml) was added bromotrimethylsilane (0.54 g, 353 μmol) and the mixture was stirred at room temperature under dry nitrogen for 18 hr. The solution was evaporated to dryness and the residue azeotroped with methanol (×3). The residue was recrystallized from methanol-water (4:1) (10 ml) to give (E)-9-(4-phosphonobut-3-enyloxy)guanine as cream coloured crystals (45 mg, 84%), m.p. >330° C.; $\lambda_{max}$ (EtOH) 255, 266nm; $v_{max}$ (KBr) 3200, 3120, 2740, 1760, 1690, 1635, 1470, 1235 and 1160 cm$^{-1}$; $\delta_H$[(CD$_3$)$_2$SO] 2.60 (2H, M, CH$_2$), 4.40 (2H, t, J 7 Hz, CH$_2$O ) 5.92 (1H, dd, J 17 Hz and 19 Hz, PCH=CH), 6.50 (1H, ddt, J 6 Hz, 17 Hz and 22 Hz, PCH=CH), 6.60 (2H, br.s, NH$_2$), 7.90 (1H, s, H-8), 10.65 (1H, br.s, H-1); FABMS (thioglycerol) 302 (MH+) (Found: C, 35.37; H, 4.01; N, 23.20%. C$_9$H$_{12}$N$_5$O$_5$P.0.2H$_2$O requires C, 35.46; H, 4.10; N, 22.98%).

EXAMPLE 2

(E)-9-[4-(Diisopropoxyphosphoryl)but-3-enyloxy]adenine a) To a mixture of 9-hydroxy-6-phthalimidopurine (141 mg, 500 μmol), diisopropyl (E)-4-hydroxybut-1-enylphosphonate (110 g, 500 μmol) and triphenylphosphine (197 mg, 750 μmol) in tetrahydrofuran (5 ml) stirred at 0° C. was added diethyl azodicarboxylate (131 mg, 750 μmol). The mixture was then stirred at room temperature for 2 hr. The solvent was removed and the residue purified by column chromatography on silica gel eluting with dichloromethane-methanol (49:1, 16:1) to give (E)-9-[4-(diisopropoxyphosphoryl)but-3-enyloxy]-6-phthalimidopurine as a gum (200 mg, 80%); $\lambda_{max}$ (EtOH) 273 (14,380) nm; $v_{max}$ (film) 2970, 1730 1590 1570 1355 1240 and 975 cm$^{-1}$; $\delta_H$[(CD$_3$)$_2$SO] 1.24 (12H, pseudo t, J 6 Hz, CH(CH$_3$)$_2$), 2.77 (2H, m, CH$_2$), 4 60 (2H, m, CH(CH$_3$)$_2$), 4.66 (2H, t, J 6 Hz, CH$_2$O ), 6.07 (1H, dd, J 17 Hz and 20 Hz, PCH=CH), 6.75 (1H, ddt, J 6 Hz, 17 Hz and 22 Hz, PCH=CH), 8.00–8.25 (4H, m, Ph), 9.00 (1H, s, H-2/H-8), 9.08 (1H, s, H-2/H-8) (Found: M+ 499.1620. C$_{23}$H$_{26}$N$_5$O$_6$P requires M+ 499.1621).

b) A mixture of (E)-9-[4-(Diisopropoxyphosphoryl)-but-3-enyloxy]-6-phthalimidopurine (186 mg, 370 μmol) and methylhydrazine (18 mg, 390 μmol) in ethanol (4 ml) was stirred at room temperature for 1.5 hr. The solvent was removed and the residue purified by column chromatography on silica gel eluting with dichloromethane-methanol (4:1) to afford (E)-9-[4-(diisopropoxyphosphoryl)but-3-enyloxy]-adenine as a gum (120 mg, 88%); $\lambda_{max}$ (EtOH) 260 (12,860)nm; $v_{max}$ (film) 3310, 3170, 2970, 1640, 1590, 1290, 1230 and 980 cm$^{-1}$; $\delta_H$[(CD$_3$)$_2$SO] 1.26 (12H, pseudo t, J 6 Hz, CH(CH$_3$)$_2$), 2.67 (2H, m, CH$_2$), 4.50 (4H, m, CH$_2$O and CH(CH$_3$)$_2$), 6.05 (1H, dd, J 17 Hz and 22 Hz, PCH=CH), 6.70 (1H, ddt, J 6 Hz, 17 Hz and 22 Hz, PCH=CH), 7.38 (2H, br.s, NH$_2$), 8.14 (1H, s, H-2/H-8), 8.36 (1H, s, H-2/H-8) (Found: M+ 369.1568. C$_{15}$H$_{24}$N$_5$O$_4$P requires M+ 369 1566).

EXAMPLE 3

(E) -9-(4-Phosphonobut-3-enyloxy)adenine

To a solution of (E)-9-[4-(diisopropoxyphosphoryl)-but-3-enyloxy]adenine (105 mg, 284 μmol) in dichloromethane was added bromotrimethylsilane (0.87 g, 5.68 mmol). The resulting white suspension was stirred at room temperature under dry nitrogen for 18 hr. The solution was evaporated to dryness and the residue azeotroped with methanol (×3). The residue was purified by column chromatography on reverse phase silica gel eluting with water to give (E)-9-(4-phosphonobut-3-enyloxy)adenine as a white solid (68 mg, 84%), m.p. 249°–251° C.; $\lambda_{max}$(MeOH) 260 (11,985)nm; $v_{max}$ (KBr) 3110, 2300, 1695, 1470, 1410, 1330 and 1030 cm$^{-1}$; $\delta_H$[(CD$_3$)$_2$SO] 2.62 (2H, m, CH$_2$), 4.50 (2t, t, J 7 Hz, CH$_2$O ), 5.94 (1H, dd, J 17 Hz and 22 Hz, PCH=CH), 6.50 (1H, ddt, J 6 Hz, 17 Hz and 22 Hz, PCH=CH), 7.39 (2H, br.s, NH$_2$), 8.16 (1H, s, H-2/H-8), 8.35 (1H, s, H-2/H-8); FABMS (thioglycerol) 286 (MH+) (Found: C, 35.75; H, 4.00; N, 23.14; Br, 5.41%. C$_9$H$_{12}$N$_5$O$_4$P.0.2HBr requires C, 35.86; H, 4.08; N, 23.24; Br, 5.30%).

EXAMPLE 4

(E)-9-[4-(Diisopropoxyphosphoryl)but-3-enyl]adenine a) To a mixture of 6-chloropurine (414 mg, 2.67 mmol), diisopropyl (E)-4-hydroxybut-1-enylphosphonate (630 mg, 2.67 mmol) and triphenyl phosphine (1.05 g, 4.00 mmol) in dry tetrahydrofuran (30 ml) stirred at 0° C. was added diethyl azodicarboxylate (0.70 g, 4.02 mmol). The mixture was allowed to warm to room temperature and stirred for 27.5 hr. The solvent was removed and the residue Was purified by column chromatography on silica gel eluting with dichloro-methane-methanol (24:1, 13:1) to give (E)-6-chloro-9-[4-(diisopropoxyphosphoryl)but-3-enyl]purine as a white solid (0.37 g, 37%), m.p. 105° C.; $\lambda_{max}$ (EtOH) 266 (9,260)nm; $\upsilon_{max}$(KBr) 3435, 2980, 1590, 1560, 1330, 1230 and 1210 cm$^{-1}$; $\delta_H$(CDCl$_3$) 1.25 (12H, dd, J 6 Hz and 21 Hz, CH(CH$_3$)$_2$), 2.88 (2H, m, CH$_2$), 4.45 (2H, t, J 7 Hz, CH$_2$N), 4.55 (2H, m, CH(CH$_3$)$_2$), 5.68 (1H, dd, J 17 Hz and 20 Hz PCH=CH), 6.70 (1H, ddt, J 7 Hz, 17 Hz and 22 Hz, PCH=CH), 8.10 (1H, s, H-2/H-8), 8.77 (1H, s, H-2/H-8); FABMS (thioglycerol) 373 (MH+) (Found: C, 48.40; H, 6.03; N, 14.81%. C$_{15}$H$_{22}$ClN$_4$O$_3$P requires C, 48.33; H, 5.95; N, 15.03%).

b) A solution of (E)-6-chloro-9-[4-(diisopropoxyphosphoryl)but-3-enyl]purine (309 mg, 829mmol) in saturated ethanolic ammonia (35 ml) was heated at 80° C. in a stainless steel autoclave for 5 hr. The solvent was removed and the residue purified by column chromatography on silica gel eluting with ethyl acetate-methanol (3:1) to give (E)-9-[4-(diisopropoxyphosphoryl)but-3-enyl]adenine as a white solid (205 mg, 70%), m.p. 121°-122° C.; $\lambda_{max}$ (EtOH) 262 (11,855)nm; $\upsilon_{max}$ (KBr) 3320, 3175, 2935, 1650. 1600, 1575, 1475 and 1240 cm$^{-1}$; $\delta_H$(CDCl$_3$) 1.25 (12H, dd, J 6 Hz and 19 Hz, CH(CH$_3$)$_2$), 2.84 (2H, m, CH$_2$), 4.35 (2H, t, J 7 Hz, CH$_2$N), 4.55 (2H, m, CH(CH$_3$)$_2$), 5.69 (1H, dd, J 17 Hz and 19 Hz, PCH=CH), 5.76 (2H, s, NH$_2$), 6.70 (1H, ddt, J 7 Hz, 17 Hz and 22 Hz, PCH=CH ), 7.79 (1H, s, H-2/H-8), 8.37 (1H, s, H-2/H-8) (Found: MH+ 354.1695. C$_{15}$C$_{24}$N$_5$O$_3$P requires MH+ 354. 1695).

EXAMPLE 5

(E)-9-[4-Phosphonobut-3-enyl]adenine

To a solution of (E)-9-[4-(diisopropoxyphosphoryl)-but-3-enyl]adenine (111 mg, 314 μmol) in dichloromethane (6 ml) was added bromotrimethylsilane (0.9 g, 6.28 mmol) and the mixture was stirred at room temperature under dry nitrogen for 18 hr. The solution was evaporated to dryness and the residue azeotroped with methanol (×3). The residue was purified by column chromatography on reverse phase silica gel eluting with water to give (E)-9-(4-phosphonobut-3-enyl)adenine as a white solid (69 mg, 81%), m.p. 263°-266° C.; $\lambda_{max}$ (MeOH) 261 (10,810)nm; $\upsilon_{max}$ (KBr) 3360, 3095, 1685, 1605, 1520, 1415,and 1228 cm$^{-1}$; $\delta_H$(D$_2$O +one drop of NH$_4$OH solution) 2.63 (2H, m, CH$_2$), 4.31 (2H, t, J 7 Hz, CH$_2$N), 5.72 (1H, pseudo-t, J 17 Hz, PCH =CH), 6.14 (1H, pseudo-tt, J 7 Hz and 17 Hz, PCH=CH), 8.13 (1H, s, H-2/H-8), 8.19 (1H, s, H-2/H-8); FABMS (thioglycerol) 270 (MH+) (Found: C, 37.29; H, 4.38; N, 24.09%. C$_9$H$_{12}$N$_5$O$_3$P.0.25HBr requires C, 37.35; H, 4.27; N, 24.20%).

EXAMPLE 6

(E)-9-(4-Phosphonobut-3-enyl) quanine a) To a mixture of 2-amino-6-chloropurine (0.6 g, 3.81 mmol) , diisopropyl (E)-4-hydroxybut-1-enylphosphonate (0.90 g, 3.81 mmol) and triphenyl phosphine (2.00 g, 7.62 mmol) in dry N,N-dimethylformamide (30 ml) stirred at 0° C. under dry nitrogen was added diethyl azodicarboxylate (1.33 g, 7.62 mmol). The mixture was allowed to warm to room temperature and stirred for 1.3 hr. The solvent was removed and the residue was purified by column chromatography on silica gel eluting with di-chloromethane-methanol (9:1) to afford (E)-2-amino-6-chloro-9-[4-(diisopropoxyphosphoryl)but-3-enyl]purine as a light brown gum (0.52 g, 35%), m.p. 150° C.; $\lambda_{max}$ (EtOH) 311 (6,760), 249 (5,420) and 224 (24,320)nm; $\upsilon_{max}$ (KBr) 3385, 3320, 3208, 1635, 1615, 1560, 1520, 1410 and 1240 cm$^{-1}$; $\delta_H$[(CD$_3$)$_2$SO] 1.08 (6H, d, J 6 Hz, CH(CH$_3$)$_2$), 1.16 (6H, d, J 6 Hz, CH(CH$_3$)$_2$), 2.77 (2H, m, CH$_2$), 4.27 (4H, m, CH$_2$N and CH(CH$_3$)$_2$), 5.69 (1H, dd, J 17 Hz and 21Hz, PCH=CH), 6.52 (1H, ddt, J 6 Hz, 17 Hz and 22 Hz PCH=CH), 6.89 (2H, br.s, D$_2$O exchangeable, NH$_2$), 8.11 (1H, s, H-8) (Found: MH+ 388.1288. C$_{15}$H$_{23}$ClN$_5$O$_3$P requires MH+ 388.1305).

b) To a suspension of (E)-2-amino-6-chloro-9-[4-(diisopropoxyphosphoryl)but-3-enyl]purine (168 mg, 433 μmol) in dichloromethane (8 ml) stirred at room temperature under dry nitrogen was added bromotrimethylsilane (1.33 g, 8.66 mmol). The mixture was stirred for 18 hr then evaporated to dryness. The residue was suspended in water (20 ml), concentrated hydrochloric acid (3 ml) added and the mixture heated at 100° C. for 1.7 hr. The solution was neutralized by addition of 2.5M sodium hydroxide solution then evaporated to dryness. The residue was purified by column chromatography on reverse phase silica gel eluting with water to give (E)-9-[4-phosphonobut-3-enyl]guanine as a white solid (66 mg, 53%), m.p. 290°-294° C. (decomp.); $\lambda_{max}$ (MeOH) 257 (8,660)nm; $\upsilon_{max}$ (KBr) 3425, 3150, 2745, 1740, 1635, 1490, 1240 and 1190 cm$^{-1}$; $\delta_H$(D$_2$O +one drop of NH$_4$OH solution) 2.62 (2H, m, CH$_2$), 4.15 (2H, t, J 7 Hz, CH$_2$N), 5.78 (1H, pseudo-t, J 17 Hz, PCH=CH), 6.15 (1H, pseudo-tt, J 7 Hz and 18 Hz, PCH=CH), 7.80 (1H, s, H-8); FABMS (thioglycerol) 286 (MH+) (Found: C, 37.25; H, 4.10; N, 24.07%. C$_9$H$_{12}$N$_5$O$_4$P.0.2H$_2$O requires C, 37.42; H, 4.32; N, 24.25%).

EXAMPLE 7

(E)-2, 6-Diamino-9-[4-(diisopropoxyphosphoryl)but-3enyl]purine

A solution of (E)-2-amino-6-chloro-9-[4-(diisopropoxyphosphoryl)but-3-enyl]purine (370 mg, 954 μmol) in saturated ethanolic ammonia (60 ml) was heated at 100° C. in a stainless steel autoclave for 7 hr. The solution was allowed to cool then the solvent was removed. The residue was purified by column chromatography on silica gel eluting with dichloromethane-methanol (19:1, 9:1) to give (E)-2, 6-diamino-9-[4-(diisopropoxyphosphoryl)but-3-enyl]purine as a white solid (175mg, 50%), m.p. 211°-213° C.; $\lambda_{max}$ (MeOH) 256 (7,860) and 283 (9,670)nm; $\upsilon_{max}$ (KBr) 3460, 3325, 3174, 1630, 1590, 1470, 1410 and 1250 cm$^{-1}$; $\delta_H$[(CD$_3$)$_2$SO] 1.11 (6H, d, J 6 Hz, CH(CH$_3$)$_2$), 1.17 (6H, d, J 6 Hz, CH(CH$_3$)$_2$), 2.50 (2H, m, CH$_2$), 4.12 (2H, t, J 7 Hz, CH$_2$N), 4.33 (2H, m, CH(CH$_3$)$_2$), 5.73 (2H, s, D$_2$O exchangeable, NH$_2$), 5.73 (1H, dd, J 17 Hz and 20 Hz, PCH=CH), 6.55 (1H, ddt, J 7 Hz, 17 Hz and 20 Hz, PCH=CH), 6.60 (2H, s, D$_2$O exchangeable, NH$_2$), 7.68 (1H, s, H-8) (Found: MH+ 369. 1803. C$_{15}$H$_{25}$N$_6$O$_3$P requires MH+ 369. 1804).

EXAMPLE 8

(E)-2,6-Diamino-9-(4-phosphonobut-3-enyl)purine

To a solution of (E)-2,6-diamino-9-[4-(diisopropoxyphosphoryl)but-3-enyl]purine (144mg, 391 μmol) in dichloromethane (10 ml) was added bromotrimethylsilane (1.20 g, 7.82 mmol) and the mixture stirred at room temperature under dry nitrogen for 18 hr. The resulting white suspension was evaporated to dryness and the residue azeotroped with methanol (×6). The residue was purified by column chromatography on reverse phase silica gel eluting with water to give a product which n.m.r. analysis showed to be the monoester. To a suspension of the monoester (approx. 306 μmol) in dry N,N-dimethylformamide (10 ml) was added bromotrimethylsilane (1.16 g, 7.58 mmol) and the resulting solution was stirred at room temperature under dry nitrogen for 18 hr. The solution was evaporated to dryness and the residue azeotroped with methanol (×3) then acetone-water (1:1) (×3). The residue was purified by column chromatography on reverse phase silica gel eluting with water to give (E)-2,6-diamino-9-(4-phosphonobut-3-enyl)purine as a white solid (30 mg, 27%), m.p. >325° C.; $\lambda_{max}$ (MeOH) 256 (6,570) and 285 (6,490)nm; $\upsilon_{max}$ (KBr) 3410, 1710, 1670, 1630, 1590, 1420, 1220 and 135 cm$^{-1}$; $\delta_H$[(CD$_3$)$_2$SO+one drop NH$_4$OH solution] 2.50 (2H, m, CH$_2$) 4.05 (2H, t, J 7 Hz, CH$_2$N), 5.70 (1H, pseudo-t, J 17 Hz, PCH=CH), 5.81 (2H, s, NH$_2$), 6.10 (1H, pseudo-tt, J 7 Hz and 20 Hz, PCH=CH), 6.69 (2H, s, NH$_2$), 7.76 (1H, s, H-8); FABMS thioglycerol) 285 (MH+).

EXAMPLE 9

(Z) -9-[4-(Diethoxyphosphoryl)but-3-enyloxy]adenine a) To a mixture of 9-hydroxy-6-phthalimidopurine (320 mg, 1.14 mmol), diethyl (Z)-4-hydroxybut-1-enylphosphonate (250 mg, 1.20 mmol) and triphenyl phosphine (448 mg, 1.71 mmol) in dry tetrahydrofuran (11 ml) stirred at 0° C. under dry nitrogen was added diethyl azodicarboxylate (296 mg, 170 mmol). The mixture was allowed to warm to r.t. and stirred for 2.3 hr. The solvent was removed and the residue was purified by column chromatography on silica gel eluting with acetone-hexane (1:1, 4:3) to give (Z)-9-[4-(diethoxyphosphoryl)but-3-enyloxy]-6-phthalimidopurine as a light brown gum (320 mg, 60%); $\lambda_{max}$ (EtOH) 271 (14,680)nm; $\upsilon_{max}$(KBr) 2980, 1735, 1595, 1575, 1360, 1330, 1245 and 1025 cm$^{-1}$; $\delta_H$[(CD$_3$)$_2$SO] 1.23 (6H, t, J 7 Hz, CH$_3$), 3.05 (2H, m, CH$_2$), 3.98 (4H, dq, J 7 Hz and 8Hz, CH$_2$CH$_3$), 4.63 (2H, t, J 6 Hz, CH$_2$O ), 5.90 (1H, dd, J 14 Hz and 20 Hz, PCH=CH), 6.75 (1H, ddt, J 7 Hz, 14 Hz and 52 Hz, PCH=CH), 8.05 (4H, m, C$_6$H$_4$), 9.05 (1H, s, H-2/H-8), 9.10 (1H, s, H-2/H-8) (Found: C, 53.77; H, 4.87; N, 14.52%; MH+ 472.1384. C$_{21}$H$_{22}$N$_5$O$_6$P requires C, 53.50; H, 4.70; N, 14.86%; MH+ 472.1386).

b) A mixture of (Z)-9-[4-(diethoxyphosphoryl)but-3-enyloxy]-6-phthalimidopurine (305 mg, 647 mmol) and methylhydrazine (31.3 mg, 679 μmol) in ethanol (7 ml) was stirred at room temperature for 1.5 hr. The solvent was removed and the residue was purified by column chromatography on silica gel eluting with dichloromethane-methanol (19:1, 9:1) to afford (Z)-9-[4-(diethoxyphosphoryl)but-3-enyloxy]adenine as a colourless gum (177 mg, 80%); $\lambda_{max}$ (EtOH) 260 (13,045) nm; $\upsilon_{max}$ (KBr) 3320, 3175, 2980, 1645, 1595, 1325, 1295 and 1240 cm$^{-1}$; $\delta_H$[(CD$_3$)$_2$SO] 1.22 (6H, t, J 7 Hz, CH$_3$), 2.95 (2H, m, CH$_2$), 3.97 (4H, pseudo qu, J 7 Hz, CH$_2$CH$_3$), 4.46 (2H, t, CH$_2$O ), 5.85 (1H, dd, J 14 Hz and 20 Hz, PCH=CH), 6.65 (1H, ddt, J 7 Hz, 14 Hz and 52Hz, PCH=CH), 7.38 (2H, br.s, NH$_2$), 8.15 (1H, s, H-2/H-8), 8.41 (1H, s, H-2/H-8) (Found: C, 45.30; H, 5.92; N, 20.17%; M+ 341.1253. C$_{13}$H$_{20}$N$_5$O$_4$P. 0.3H$_2$O requires C, 45.03; H, 5.96; N, 20.20%; M+ 341.1253).

EXAMPLE 10

(Z)-9-(4-Phosphonobut-3-enyloxy) adenine

To a solution of (Z)-9-[4-(diethoxyphosphoryl)-but-3-enyloxy]adenine (145 mg, 425 μmol) in dichloromethane (10 ml) was added bromotrimethylsilane (1.29 g, 8.48 mmol) and the resulting solution was stirred at room temperature under dry nitrogen for 18 hr. The solvent was removed and the residue was azeotroped with methanol (×5). The residue was purified by column chromatography on reverse phase silica gel eluting with water to give (Z)-9-(4-phosphonobut-3-enyloxy]adenine as a white solid (98 mg, 81%), m.p. 238° C.; $\lambda_{max}$ (MeOH) 260 (13,515)nm; $\upsilon_{max}$ (KBr) 3420, 3200, 3085, 2970, 1700, 1610, 1485, 1415 and 1335 cm$^{-1}$; $\delta_H$[(CD$_3$)$_2$SO] 2.94 (2H, m, CH$_2$), 4.43 (2H, t, J 7 Hz, CH$_2$O ), 5.77 (1H, dd, J 14 Hz and 17 Hz, PCH=CH), 6.40 (1H, ddt, J 7 Hz, 14 Hz and 47 Hz, PCH=CH), 7.40 (2H, br.s, NH$_2$). 8.15 (1H, s, H-2/H-8), 8.42 (1H, s, H-2/H-8); FABMS (thioglycerol) 286 (NH+) (Found: C, 36.71; H, 4.16; N, 23.96%. C$_9$H$_{12}$N$_5$O$_4$P.0.4H$_2$O requires C, 36.96; H, 4.41; N, 23.95%).

EXAMPLE 11

(Z)-9-(4-Phosphonobut-3-enyloxy)quanine a) To a mixture of 2-[di-(t-butoxycarbonyl]-amino-9-hydroxy-6-methoxypurine (487 mg, 1.28 mmol), diethyl (Z)-4-hydroxybut-1-enylphosphonate (266 mg, 1.28 mmol) and triphenyl phosphine (504 mg, 1.92 mmol) in dry tetrahydrofuran (15 ml) stirred at 0° C. under dry nitrogen was added diethyl azodicarboxylate (332 mg, 1.91 mmol). The mixture was allowed to warm to room temperature and stirred for 1.5 hr. The solvent was removed and the residue was purified by column chromatography on silica gel eluting with acetone-hexane (1:1) to give (Z)-2-[di-t-butoxycarbonyl]amino-9-[4-(diethoxyphosphoryl)-but-3-enyloxy]-6methoxypurine as a colourless gum (443 mg, 61%); $\lambda_{max}$ (EtOH) 256 (10,920)nm; $\upsilon_{max}$ (KBr) 2980, 2360, 1790, 1760, 1590, 1475, 1370, 1280 and 1255cm$^{-1}$; $\delta_H$[(CD$_3$)$_2$SO] 1.21 (6H, t, J 7 Hz, CH$_2$CH$_3$), 1.40 (18H, s, C(CH$_3$)$_3$), 2.97 (2H, m, CH$_2$), 3.95 (4H, pseudo qu, J 7 Hz, CH$_2$CH$_3$), 4.50 (2H, t, J 7 Hz, CH$_2$O ), 5.83 (1H, dd, J 4 Hz and 19 Hz, PCH=CH), 6.68 (1H, ddt, a. 7 Hz, 14 Hz and 52 Hz, PCH=CH), 8.75 (1H, s, H-8); CIMS (ammonia) 572 (MH+) (Found: C, 50.16; H, 6.63; N, 12.63%. C$_{24}$H$_{35}$N$_5$O$_9$P requires C, 50.43; H, 6.70; N, 12.25%).

b) To a solution of (Z)-2-[di-(t-butoxycarbonyl)]-amino-9-[4 -(diethoxyphosphoryl)but-3-enyloxy ] 6-methoxypurine (270 mg, 472 μmol) in dichloromethane (15 ml) was added bromotrimethylsilane (1.44 g, 9.44 mmol) and the mixture was stirred at room temperature under dry nitrogen for 18 hr. The solution was evaporated to dryness and the residue azeotroped with methanol (×1) then acetone-water (1:1) (×3). The residue was suspended in water and warmed on a steam bath. The mixture was cooled and purified by column chromatography on reverse phase Silica gel eluting with water to afford (Z)-9-(4-phosphonobut-3-enyloxy)guanine as a white solid (60 mg, 42%), m.p. 240°–242° C.; $\lambda_{max}$(MeOH) 255 (13,000)nm; $\upsilon_{max}$(KBr) 3390, 3140, 1695, 1650, 1610, 1475, 1385 and 1165 cm$^{-1}$; $\delta_H$[(CD$_3$)$_2$SO] 2.91 (2H, m, CH$_2$), 4.32 (2H, t, J 7 Hz, CH$_2$O ), 5.75 (1H, dd, J 13 Hz and 17 Hz, PCH=CH), 6.30 (1H, ddt, J 7 Hz, 13 Hz and 47 Hz, PCH=CH), 6.61 (2H, br.s, D$_2$O exchangeable, NH$_2$), 7.95 (1H, s, H-8), 10.63 (1H, br.s, D$_2$O exchangeable, H-1); FABMS (thioglycerol) 302 (MH$^+$) (Found: C, 35.07; H, 3.79; N, 22.48%. C$_9$H$_{12}$N$_5$O$_5$P.0.4H$_2$O requires C, 35.05; H, 4.18; N, 22.71%).

EXAMPLE 12

(E)-9-[4-Diisopropoxyphosphoryl)-2-(hydroxymethyl)but-3-enyloxy]quanine a) A mixture of 2-[di-(t-butoxycarbonyl)]amino-9-hydroxy-6-methoxypurine (0.62 g, 1.6 mmol), triphenylphosphine (0.43 g, 1.6 mmol), and diisopropyl (E)-3-(t-butyldiphenylsilyloxy)methyl-4-hydroxybut-1-enylphosphonate (0.6 g, 1.2 mmol) in anhydrous THF (15 ml) at 0° C. was treated dropwise, slowly, with diethyl azodicarboxylate (0.25 g, 1.6 mmol). After stirring overnight at room temperature, the solvent was removed in vacuo and the residue chromatographed on silica gel, eluting with acetone-hexane (1:2) to give (E)-9-[2-(t-butyldiphenylsilyloxy)methyl-4(diisopropoxyphosphoryl)but-3-enyloxy]-2-[di-(t-butoxycarbonyl)]amino-6-methoxypurine as a gum (0.7 g, 66%); $\upsilon_{max}$ (KBr) 2977, 2932, 2858, 1792, 1757, 1734, 1592, 1472, and 1427 cm$^{-1}$; $\delta_H$(CDCl$_3$) 1.06 [9H, s, C(CH$_3$)$_3$], 1.30 [12H, s, 2×CH(CH$_3$)$_2$], 1.43 [18H, s, 2×C(CH$_3$)$_3$], 2.92 (1H, CH), 3.85 (2H, m, CH$_2$), 4.15 (3H, s, OCH$_3$), 4.4–4.75 [4H, CH$_2$, 2×CH (CH$_3$)$_2$], 5.91 (1H, ddd, J 1, 17 and 19 Hz, PCH=CH), 6.77 (1H, ddd, J 8, 17 and 25Hz, PCH=H), 7.3–7.85 (11H, m, 2×C$_6$H$_5$, H-8) (Found: C, 59.77; H, 7.52;N, 7.79%. C$_{43}$H$_{62}$N$_5$O$_{10}$PSi requires C, 59.50; H, 7.20; N, 8.07%).

b) A solution of (E)-9-[2-(t-butyldiphenylsilyloxy)-methyl-4-(diisopropoxyphosphoryl)but-3-enyloxy]-2-[di-(t-butoxycarbonyl)]amino-6-methoxypurine (0.45 g, 0.5 mmol) in ethanol (10 ml) and 5M hydrochloric acid (1 ml, 5 mmol) was heated under reflux for 4.5 h. The solvent was removed in vacuo and the residue was chromatographed on silica gel eluting with chloroform-methanol (10:1) to give the title compound as a solid (0.16 g, 74%); $\upsilon_{max}$ 3381, 3160, 2981, 2935, 2751, 1685, 1632, 1596,and 1472 cm$^{-1}$; $\delta_H$ [(CD$_3$)$_2$SO] 1.22 [12H, m, 2×(CH$_3$)$_2$CH], 2.82 (1H, m, CH), 3.57 (2H, m, CH$_2$), 4.3–4.6 [4H, m, 2×(CH$_3$)$_2$CH plus CH$_2$ON], 4.91 (1H, t, J 5 Hz, D$_2$O exchangeable OH), 6.00 (1H, ddd, J 1, 17 and 18 Hz, PCH=CH), 6.65 (3H, m, D$_2$O exchangeable NH$_2$ plus PCH=CH), 7.87 (1H, s, H-8), 10.69 (1H, s, D$_2$O exchangeable H-1).

EXAMPLE 13

(E)-9-(2-Hydroxymethyl-4 -phosphonobut-3-enyloxy)quanine

A solution of (E)-9-[4-(E)-diisopropoxyphosphoryl)-2-(hydroxymethyl)but-3-enyloxy]guanine (0.16 g, 0.38 mmol) in anhydrous N,N-dimethylformamide (4 ml) under nitrogen at 0° C. was treated with trimethylsilyl-bromide (0.76 ml, 5.8 mmol), and the solution stirred at room temperature for 18 h. The solvent was removed in vacuo coevaporating several times with methanol and methanol-toluene mixtures. The resulting gum was purified by chromatography twice on C18 reverse phase silica gel to give (E)-9-(2-hydroxymethyl-4-phosphonobut-3-enyloxy)guanine as a solid (22 mg, 17%), $\lambda_{max}$ (H$_2$O) 253nm (12,277); $\upsilon_{max}$ (KBr) 3422, 3125, 2922, 2852, 2752, 1691, 1639, 1611, 1552, 1533, 1474, and 1451 cm$^{-1}$; $\delta_H$[(CD$_3$)$_2$SO] 2.70 (1H, m, CH), 3.30 (>3H, br.s, D$_2$O exchangeable OH's, plus H$_2$O), 3.55 (2H, m, CH$_2$OH), 4.35 (2H, m, CH$_2$ON), 5.95 (1H, dd, J$_1$=J$_2$=17.9 Hz, PCH=CH), 6.45 (1H, m, PCH=CH), 6.60 (2H, br.s, D$_2$O exchangeable NH$_2$), 7.85 (1H, s, H-8), 10.63 (1H, br.s, H-1) (Found: C, 35.50; H, 4.27; N, 20.96% C$_{10}$H$_{14}$N$_5$O$_6$P.0.4H$_2$O requires C, 35.49; H, 4.41; N, 20.69%).

EXAMPLE 14

(E)-9-[4-(Diisopropoxyphosphoryl)-2-(hydroxymethyl)but-3-enyloxy]adenine a) A mixture of 9-hydroxy-6-phthalimidopurine (0.94 g, 3.4 mmol), diisopropyl (E)-3-t-(butyldiphenylsilyloxy)methyl4-hydroxybut-1-enylphosphonate (1.3 g, 2.6 mmol) and triphenylphosphine (0.88 g, 3.4 mmol) at 0° C. in anhydrous THF (20 ml) was treated dropwise, slowly with diethyl azodicarboxylate (0.53 g, 3.4 mmol) in anhydrous THF (5 ml). After stirring overnight at room temperature, the solvent was removed and the residue chromatographed on silica gel eluting with ethyl acetate-hexane (1:1), increasing polarity to ethyl acetate, to give (E)-9-[2-(t-butyldiphenylsilyloxy)-methyl-4-(diisopropoxyphosphoryl)but-3-enyloxy]-6-phthalimidopurine as a glass (1.22 g, 62%); $\upsilon_{max}$ 3447, 3071, 2978, 2931, 2858, 1792, 1737, 1598, 1577, 1468, 1455, 1428,and 1406 cm$^{-1}$; $\delta_H$(CDCl$_3$) 1.07 [9H, s, C(CH$_3$)$_3$], 1.29 (3H, d, J 6 Hz, CH$_3$CH), 1.30 (3H, d, J 6 Hz, CH$_3$CH), 1.34 [6H, d, J 6 Hz, (CH$_3$)$_2$CH], 3.0 (1H, s, CH), 3.90 (2H, m, CH$_2$), 4.70 (4H, m, CH$_2$, 2×CH(CH$_3$)$_2$], 6.00 (1H, ddd, J 1.4, 17.3 and 19.0 Hz, PCH=CH), 6.81 (1H, ddd, J 7, 17, and 22 Hz, PCH=CH), 7.3–8.2 (15H, m, C$_6$H$_4$, 2×C$_6$H$_5$, H-2/H-8), 9.04 (1H, s, H-2/H-8) (Found: C, 61.58; H, 6.09; N, 8.56%. C$_{40}$H$_{46}$N$_5$O$_7$PSi requires C, 61.84; H, 6.10; N, 9.01%).

b) A solution of (E)-9-[2-(t-butyldiphenylsilyloxy)-methyl-4-(diisopropoxyphosphoryl)but-3-enyloxy]-6-phthalimidopurine (1.17 g, 1.5 mmol) in dichloromethane (25 ml) at 0° C. was treated dropwise with methyl hydrazine (0.12 ml, 2.2 mmol). After stirring at room temperature for 1h, the solvent was removed in vacuo and the residue was dissolved in acetone-hexane (1:1) (30 ml). After filtration of the insoluble white solid, the solvent was removed in vacuo and the residue chromatographed on silica gel, eluting with acetone-hexane (1:1) increasing polarity to (2:1) to give (E)-9-[2-(t-butyldiphenylsilyloxy)methyl-4-(diisopropoxyphosphoryl)but-3-enyloxy]adenine as a gum (0.72 g, 74%); $\upsilon_{max}$ (KBr) 3325, 3175, 2978, 2931, 2858, 2230, 641, 1593, 1471, 1427, and 1415 cm$^{-1}$; $\delta_H$ (CDCl$_3$) 1.04 [9H, s, C(CH$_3$)$_3$], 1.27 (3H, d, J 6 Hz, CH$_3$CH), 1.28 (3H, d, J 6 Hz, CH$_3$CH), 1.33 [6H, d, J 6 Hz, (CH$_3$)$_2$CH], 2.92 (1H, m, CH), 3.85 (2H, m, CH$_2$), 4.47–4.75 [4H, m, 2×CH(CH$_3$)$_2$, CH$_2$ON], 5.69 (2H, s, D$_2$O exchangeable NH$_2$), 5.9(1H, ddd, J 1.4, 17.3 and 19.2 Hz, PC$\underline{H}$=CH), 6.78 (1H, ddd, J 7, 17 and 22 Hz, PCH=C$\underline{H}$), 7.3–7.75 (11H, m, 2×C$_6$H$_5$, H-2/H-8), 8.34 (1H, s, H-2/H-8) (Found: MH+ 638.2909 C$_{32}$H$_{44}$N$_5$O$_5$PSi requires MH+ 638.2928).

c) A solution of ($\underline{E}$)-9-[2-(t-butyldiphenylsilyloxy)-methyl-4-(diisopropoxyphosphoryl)but-3-enyloxy]adenine (0.27 g, 0.4 mmol) in 3% methanolic hydrogen chloride (5 ml) was heated at 60° C. for 5.5 h. The solvent was removed in vacuo and the residue chromatographed on silica gel eluting with chloroform-methanol (20:1) increasing polarity to (10:1) to give the title compound as a glass (0.14 g, 83%); υ$_{max}$ 3391, 3204, 2980, 2934, 1689, 1642, 1599, 1468 and 1400 cm$^{-1}$; δ$_H$[(CD$_3$)$_2$SO] 3.60 (>3H, m, CH$_2$, D$_2$O exchangeable OH), 4.55 [4H, m, 2×C$\underline{H}$(CH$_3$)$_2$, CH$_2$ON], 6.07 (1H, ddd, J 1, 17 and 18 Hz, PC$\underline{H}$=CH), 6.65 (1H, ddd, J 7, 17 and 23 Hz, PCH=C$\underline{H}$), 7.80 (2H, s, D$_2$O exchangeable NH$_2$), 8.23 (1H, s, H-2/H-8), 8.46 (1H, s, H-2/H-8H) (Found: C, 40.27; H, 5.62; N, 14.37%. C$_{16}$H$_{26}$N$_5$O$_5$P.0.85CHCl$_3$ requires C, 40.41; H, 5.40; N, 14.00%).

EXAMPLE 15

(E) -9-(2-Hydroxymethyl-4-phosphonobut-3-enyloxy)adenine

A solution of ($\underline{E}$)-9-[4-(diisopropoxyphosphoryl) -2(hydroxymethyl)but-3-enyloxy]adenine (0.25 g, 0.63 mmol) in anhydrous N,N-dimethylformamide (5 ml) under nitrogen was treated with trimethylsilylbromide (1.24 ml, 9.4 mmol) at 0° C. and the solution stirred for 18 h at room temperature. The solvent was removed in vacuo coevaporatng several times with methanol and toluene and the residue chromatographed on C18 reverse phase silica gel eluting with water to give ($\underline{E}$)-9-(2-hydroxymethyl-4-phosphonobut-3-enyloxy) adenine as a solid (30 g, 17%); λ$_{max}$ (H$_2$O) 260 nm (13711); υ$_{max}$ (KBr) 3434, 1717, 1690, 1653, 1640, 1472, and 1414 cm$^{-1}$; δ$_H$[(CD$_3$)$_2$SO] 2.78 (1H, m, CH), 3.38 (3H, br.s, 3×OH, H$_2$O), 3.60 (2H, m, C$\underline{H}_2$OH) , 4.48 (2H, m, CH$_2$ON), 5.99 (1H, m, PC$\underline{H}$=CH), 6.48 (1H, m, PCH=C$\underline{H}$), 7.37 (2H, br.s, D$_2$O exchangeable NH$_2$), 8.14 (1H, s, H-2/H-8), 8.34 (1H, s, H-2/H-8) (Found: C, 36.50; H, 4.45; N, 20.49%. C$_{10}$H$_{14}$N$_5$O$_5$P.0.9H$_2$O requires C, 36.24; H, 4.77; N, 21.13%).

EXAMPLE 16

(E)-9-[4-(Diisopropoxyphosphoryl)-2-(hydroxymethyl)but-3enyl]adenine a) To a solution of 6-chloropurine (213 mg, 1.37 mmol), diisopropyl ($\underline{E}$)-3-(t-butyldiphenylsilyloxy)methyl-4-hydroxybut-1-enylphosphonate (694 mg, 1.37 mmol) and triphenyl phosphine (540 mg, 2.06 mmol) in N,N-dimethylformamide (22 ml) stirred at 0° C. under dry nitrogen was added diethyl azodicarboxylate (358 mg, 2.06 mmol). The solution was stirred at room temperature for 16 h. The solvent was removed and the residue purified by column chromatography on silica gel eluting with acetone-hexane (1:4, 1:2) then ethyl acetate-methanol (99:1, 9:1) to give (E)-9-[2-(t-butyldiphenylsilyloxy) methyl-4-(diisopropoxyphosphoryl)but-3-enyl]-6-chloropurine as a colourless gum (244 mg, 28%); λ$_{max}$ (EtOH) 265 (9,215nm; υ$_{max}$ (film) 2980, 2930, 1590, 1560, 1425, 1385, 1335 and 1245 cm$^{-1}$; δ$_H$(CDCl$_3$) 1.10 (9H, s, CH$_3$), 1.20 (12H, m, CH (CH$_3$)$_2$), 3.07 (1H, m, CH), 3.69 (2H, d, J 6 Hz, CH$_2$O ), 4.50 (4H, m, CH$_2$N and C$\underline{H}$(CH$_3$)$_2$), 5.57 (1H, pseudo-t, J 17 Hz, PC$\underline{H}$=CH), 6.66 (1H, ddd, J 8 Hz, 17 Hz and 26 Hz, PCH=C$\underline{H}$), 7.30–7.70 (10H, m, Ph), 8.00 (1H, s, H-2/H-8), 8.73 (1H, s, H-2/H-8) (Found: M+ 641.2459. C$_{32}$H$_{42}$N$_4$ClO$_4$PSi requires M+ 641.2479).

b) A mixture of ($\underline{E}$)-6-chloro-9-[2-(t-butyldiphenylsilyloxy)methyl-4-(diisopropoxyphosphoryl)but-3-enyl]purine (244 mg, 381 μmol) and sodium azide (25 mg, 381 μmol) in N,N-dimethylformamide (7 ml) was heated at 70° C. for 2.8 h. The solvent was removed and the residue purified by column chromatography on silica gel eluting with acetone-hexane (1:4, 1:1) to give ($\underline{E}$)-6-azido-9-[2-(t-butyldiphenylsilyloxy)methyl-4-(diisopropoxyphosphoryl)but-3-enyl]purine as a gum (186 mg, 75%); λ$_{max}$ (EtOH) 282 (10,363)nm; υ$_{max}$ (film) 2980, 2935, 2155, 1640, 1375, 1250 and 1110 cm$^{-1}$; δ$_H$ (CDCl$_3$) 1.00–1.40 (21H, m, CH$_3$), 3.05 (1H, m, CH), 3.70 (2H, m, CH$_2$O ), 4.30–4.80 (4H, m, CH$_2$N and C$\underline{H}$(CH$_3$)), 5.58 (1H, m, PC$\underline{H}$=CH) , 6.70 (1H, m, PCH=C$\underline{H}$) , 7.30–7.70 (10H, m, C$_6$H$_5$) , 7.86 (0.35H, s, H-2/H-8), 8.05 (0.65H, s, H-2/H-8), 8.64 (0.35H, s, H-2/H-8), 9.44 (0.65H, s, H-2/H-8)*; FABMS (TDE/Na) 670 (MNa+), 648 (MH+).

* Mixture of Azido and Tetrazolo Tautomers c) A solution of ($\underline{E}$)-6-azido-9-[2-(t-butyldiphenylsilyloxy)-methyl-4-(diisopropoxyphosphoryl)but-3-enyl]purine (320 mg, 494 μmol) and triphenylphosphine (194 mg, 741 μmol) in tetrahydrofuran (15 ml) was stirred at room temperature for 21 h. The solution was heated to 70° C. and 5M hydrochloric acid (258 μl, 1.29 mmol) added. After 2 h, the solvent was removed and the residue was dissolved in 3% methanolic hydrogen chloride (10 ml) and the solution stirred at room temperature for 2 h. The solvent was removed, the residue dissolved in water and the solution neutralised by addition of aqueous sodium bicarbonate solution. The solution was evaporated to dryness and the residue purified by column chromatography on silica gel eluting with dichloromethane-methanol (9:1, 6:1) to give the title compound as a white solid (124 mg, 63%), m.p. 130° C.; λ$_{max}$ (EtOH) 261 (13,074)nm; υ$_{max}$ (KBr) 3325, 2980, 1645, 1600, 1475, 1420, 1240 and 990 cm$^{-1}$; δ$_H$ [(CD$_3$)$_2$SO] 1.10 (12H, m, CH$_3$), 3.07 (1H, m, CH), 3.50 (2H, t, J 5Hz, CH$_2$O), 4.10 (1H, m, CH(CH$_3$)$_2$)), 4.27 (3H, m, CH$_2$N and C$\underline{H}$(CH$_3$)$_2$), 4.99 (1H, t, J 5Hz, D$_2$O exchangeable, OH), 5.59 (1H, dd, J 17 Hz and 21 Hz, PC$\underline{H}$=CH), 6.52 (1H, ddd, J 8 Hz, 17 Hz and 22 Hz, PC$\underline{H}$=CH), 7.16 (2H, br.s, D$_2$O exchangeable, NH$_2$), 8.07 (1H, s, H-2/H-8), 8.12 (1H, s, H-2/H-8); CIMS 384 (MH+) (Found: C, 48.92; H, 6.90; N, 17.58%. C$_{16}$H$_{26}$N$_5$O$_4$P.0.5 H$_2$O requires C, 48.97; H, 6.94; N, 17.85%).

EXAMPLE 17

(E)-9-(2-Hydroxymethyl-4-phosphonobut-3-enyl)adenine

A solution of (E)-9-[2-hydroxymethyl-4-(diisopropoxyphosphoryl)but-3-enyl]adenine (107 mg, 280 μmol) and bromotrimethylsilane (0.86 g, 5.61 mmol) in N,N-dimethylformamide (5 ml) was stirred at room temperature under dry nitrogen for 18 h. The solvent was removed and the residue azetroped with methanol (×3). The residue was purified by column chromatography on reverse phase silica gel eluting with water to give (E)-9-(2-hydroxymethyl-4-phosphonobut-3-enyl)adenine as a white solid (34 mg, 40%), m.p. >300° C.; $\lambda_{max}$ (MeOH) 262 (10,704)nm; $\upsilon_{max}$ (KBr) 3435, 1695, 1640, 1415, 1263, 1229 and 1030 cm$^{-1}$; $\delta_H$ [(CD$_3$)$_2$SO/D$_2$O] 2.73 (1H, m, CH), 3.37 (2H, d, J 6 Hz, CH$_2$O), 4.13 (1H, dd, J 7 Hz and 14 Hz, CH$_2$N), 4.30 (1H, dd, J 7 Hz and 14 Hz, CH$_2$N), 5.65 (1H, pseudo-t, J 17 Hz, PCH=CH), 6.06 (1H, ddd, J 8Hz, 19 Hz, PCH=CH), 8.10 (1H, s, H-2/H-8), 8.17 (1H, s, H-2/H-8); FABMS (thioglycerol) 300 (MH+) (Found: C, 37.83; H, 4.83; N, 21.75%. C$_{10}$H$_{14}$N$_5$O$_4$P.H$_2$O requires C, 37.86; H, 5.08; N, 22.07%).

EXAMPLE 18

(E)-9-(2-Hydroxymethyl-4-phosphonobut-3-enyl)quanine a) To a solution of 2-acetamido-6-chloropurine[1] (326 mg, 1.54 mmol) diisopropyl (E)-3-(t-butyldiphenylsilyloxy)-methyl-4-hydroxybut-1-enylphosphonate (775 mg, 1.54 mmol) and triphenyl phosphine (606 mg, 2.31 mmol) in N,N-dimethylformamide, stirred at 0° C. under dry nitrogen, was added diethyl azodicarboxylate (0.40 g, 2.31 mmol). The solution was stirred at room temperature for 16 h. The solvent was removed and the residue purified by column chromatography on silica gel eluting with ethyl acetate then ethyl acetatemethanol (19:1) to give (E)-2-acetamido-9-[2-(t-butyldiphenylsilyloxy)methyl-4-(diisopropoxyphosphoryl)but-3-enyl]-6-chloropurine as a colourless gum (390 mg, 36%); $\lambda_{max}$ (EtOH) 224 (29,735), 260 (8,593) and 289 (9,915)nm; $\upsilon_{max}$(KBr) 2980, 2930, 1695, 1610, 1575, 1515, 1375, 1285 and 1235 cm$^{-1}$; $\delta_H$(CDCl$_3$) 1.09 (9H, s, C(CH$_3$)$_3$), 2.53 (3H, s, NCOCH$_3$), 3.00 (1H, m, CH), 3.67 (2H, m, CH$_2$O), 4.25–4.60 (4H, m, CH$_2$N and CH(CH$_3$)$_2$), 5.58 (1H, pseudo-t, J 18 Hz, PCH=CH), 6.67 (1H, ddd, J8 Hz, 17 Hz and 22 Hz, PCH=CH), 7.50 (10H, m, C$_6$H$_5$), 7.86 (1H, s, H-8), 8.29 (1H, br.s, D$_2$O exchangeable, NH) (Found: M+ 698.2697. C$_{34}$H$_{45}$N$_5$O$_5$ClPSi requires M+ 698.2695).

1. W. A. Bowles et al., *J. Med. Chem.*, 1963, 6, 471.

b) A solution of (E)-2-acetamido-9-[2-(t-butyldiphenylsilyloxy)methyl-4-(diisopropoxyphosphoryl)but-3-enyl]-6-chloropurine (330 mg, 473 μmol) in 7% methanolic hydrogen chloride (15 ml) was stirred at room temperature for 7 h. The solution was reduced to ¼ volume then neutralised by addition of saturated sodium bicarbonate solution. The solvent was removed and the residue purified by column chromatography on silica gel eluting with dichloromethane-methanol (19:1, 6:1) to give (E)-2-amino-9-[4-(diisopropoxyphosphoryl)-2-(hydroxymethyl)but-3-enyl]-6-methoxypurine as a colourless gum (140 mg, 72%); $\lambda_{max}$ (EtOH) 249 (8,632) and 283 (9,086)nm; $\upsilon_{max}$ (KBr) 3335, 2980, 1610, 1585, 1475, 1410, 1400 and 1250 cm$^{-1}$; $\delta_H$ [(CD$_2$)$_2$SO] 1.10 (12H, m, CH(CH$_3$)$_2$), 3.02 (1H, m, CH), 3.50 (2H, t, J 5 Hz, CH$_2$O), 3.94 (3H, s, CH$_3$O), 4.10–4.40 (4H, m, CH$_2$N and CH(CH$_3$)$_2$), 4.97 (1H, t, J 5 Hz, D$_2$O exchangeable, OH), 5.61 (1H, dd, J 17 Hz and 20 Hz, PCH=CH), 6.43 (2H, br.s, D$_2$O exchangeable, NH$_2$), 6.50 (1H, ddd, J 8 Hz, 17 Hz and 22 Hz, PCH=CH), 7.80 (1H, s, H-8) (Found: MH+ 414. 1900). C$_{17}$H$_{28}$N$_5$O$_5$P requires MH+ 414.1906).

c) A solution of (E)-2-amino-9-[4-(diisopropoxyphosphoryl)-2-(hydroxymethyl)but-3-enyl]-6-methoxypurine (135 mg, 327 μmol) and bromotrimethylsilane (1.0 g, 6.53 mmol) in N,N-dimethylformamide (5 ml) was stirred at room temperature under dry nitrogen for 18 h. The solvent was removed and the residue azeotroped with methanol (×3). The residue was purified by column chromatography on reverse phase silica gel eluting with water to give the title compound as a white solid (42 mg, 40%), m.p. >300° C.; $\lambda_{max}$ (MeOH) 256 (7,402) nm; $\upsilon_{max}$ (KBr) 3425, 1715, 1640, 1610, 1480, 1410, 1380 and 1160 cm$^{-1}$; $\delta_H$ [(CD$_3$)$_2$SO] 2.80 (1H, m, CH), 3.40 (2H, d, J 5 Hz, CH$_2$O), 4.04 (2H, m, CH$_2$N), 5.73 (1H, pseudo-t, H 18 Hz, PCH=CH), 6.35 (1H, ddd, J 7 Hz, 17 Hz and 22 Hz, PCH=CH), 6.50 (2H, br.s, D$_2$O exchangeable, NH$_2$), 7.60 (1H, s, H-8), 10.56 (1H, br.s, D$_2$O exchangeable, H-1); FABMS (thioglycerol) 316 (MH+) (Found: C, 38.20; H, 4.82; N, 21.58%. C$_{10}$H$_{14}$N$_5$O$_5$P.0.2H$_2$O.0.2 DMF requires C, 38.19; H, 4.77; N, 21.84%).

Antiviral Activity

1. Plaque Reduction Test for Herpes Simplex Viruses 1 and 2

MRC-5 cells were grown to confluence in 24 well multi-dishes (well diameter=1.5 cm). The drained cell monolayers were each infected with approximately 50 infectious particles of herpes simplex virus 1 (HSV-1; strain SC16) or herpes simplex virus 2 (HSV-2; strain MS) in 100 μl of phosphate-buffered saline. The virus was adsorbed for 1 hour at room temperature. After adsorption, residual inoculum was removed from each well and replaced with 0.5 ml of Eagle's MEM containing 5% newborn calf serum and 0.9% agarose (A37). Once the agarose had set, dilutions of the test compound, which had been prepared in Eagle's MEM (containing 5% newborn calf serum), were added, each well receiving 0.5 ml of liquid overlay. The test compound was diluted to give the following series of concentrations: 200, 60, 20, 6 . . . 0.06 μg/ml; final concentrations in the assay ranged, therefore, between 100 μg/ml and 0.03 μg/ml. The infected cultures were incubated at 37° C. in a humidified atmosphere of 5% CO$_2$ until plaques were clearly visible (usually 1 day).

2. Plaque Reduction Test for Varicella-Zoster Virus

MRC-5 cells were grown to confluence in 24 well multi-dishes (well diameter=1.5 cm). The drained cell monolayers were each infected with approximately 50 infectious particles of varicella zoster virus (VZV; Ellen strain) in 100 μl of phosphate-buffered saline. The virus was adsorbed for 1 hour at room temperature. After adsorption, residual inoculum was removed from each well and replaced with 0.5 ml of Eagle's MEM containing 5% heat-inactivated foetal calf serum and 0.9% agarose (A37). Once the agarose had set, dilutions of the test compound, which had been prepared in Eagle's MEM (containing 5% heat-inactivated foetal calf serum), were added, each well receiving 0.5 ml of liquid overlay. The test compound was diluted to give the following series of concentrations: 200, 60, 20, 6 . . . 0.06 μg/ml; final concentrations in the assay ranged, therefore, between 100 μg/ml and 0.03 μg/ml. The infected cultures were incubated at 37° C. in a humidified atmosphere of 5% CO$_2$ until plaques were clearly visible (5 or 6 days).

Cultures from 1 and 2 were fixed in formal saline, the agarose overlays were carefully washed off, and then the cell monolayers were stained with carbol fuchsin. A stereo microscope was used to count plaques. The IC$_{50}$ (concentration of drug which inhibits the number of plaques formed by 50% relative to the number of plaques observed in virus control monolayers) of the test compound was calculated. In addition, the monolayers were examined for evidence of drug-induced cytotoxicity; the minimum concentration at which cytotoxicity occurs was recorded.

3. Plaque Reduction Test for Cytomegalovirus

MRC-5 cells were grown to confluence in 24 well multi-dishes (well diameter=1.5 cm). The drained cell monolayers were each infected with approximately 50 infectious particles of cytomegalovirus (CMV; AD-169 strain) in 100 μl of phosphate-buffered saline. The virus was adsorbed for 1 hour at room temperature. After adsorption, residual inoculum was removed from each well and replaced with 1 ml of Eagle's MEM containing 10% heat inactivated foetal calf serum and 0.9% agarose (A37). Once the agarose had set, dilutions of the test compound, which had been prepared in Eagle's MEM (containing 10% heat-inactivated calf serum), were added, each well receiving 1 ml of liquid overlay. The test compound was diluted to give the following series of concentrations: 200, 60, 20, 6 . . . 0.06 μg/ml; final concentrations in the assay range, therefore, between 100 μg/ml and 0.03 μg/ml. The infected cultures were incubated at 37° C. in a humidified atmosphere containing 5% $CO_2$ until plaques were clearly visible (about 12 days). The cultures are fixed in formol saline, the agarose overlays were carefully washed off, and then the cell monolayers were stained with carbol fuchsin. A stereo microscope was used to count plaques. The IC$_{50}$ (concentration of drug which inhibits the number of plaques formed by 50% relative to the number of plaques observed in virus control monolayers) of the test compound was calculated. In addition, the monolayers were examined for evidence of drug-induced cytotoxicity; the minimum concentration at which cytotoxicity occurs was recorded.

4. CPE Inhibition Test (Established Monolayer) for Lentiviruses $3 \times 10^4$ sheep choroid plexus (SCP) cells were plated into individual wells of a 96 well microtitre plate in 100 μl of Eagle's MEM with Hanks' salts containing 10% heat inactivated foetal calf serum (FCS). When monolayers had become established (after 1 or 2 days growth) they were washed with 200 μl of maintenance medium (Eagle's MEM with Hanks' salts containing 0.5% FCS) and infected with 100 μl of visna virus (strain K184) in maintenance medium (30 TCID50/ml). Test samples were diluted with maintenance medium in further 96 well microtitre plates over the range 200–0.06 μg/ml by 3-fold dilution steps. 100 μl of the diluted samples was then transferred directly onto virus-infected monolayers (final concentration range therefore 100–0.03 μg/ml) and incubated at in a humidified atmosphere containing 5% $CO_2$ until virus-induced CPE was maximal in the untreated virus-infected controls (usually 12–14 days). The plates were fixed with formal saline and stained with crystal violet. Virus-induced CPE was then scored microscopically and the minimum concentration of sample giving complete protection of the cell monolayers (MIC) determined.

5. Test for Human Immunodeficiency Virus (HIV)

a) Cell cytotoxicity test

Peripheral human lymphocytes were isolated by density gradient centrifugation from blood donations of healthy volunteers. The 'buffy coat'-fractions of these donations were provided by blood donation centres.

The buffy coat was diluted 1:1 with sterile phosphate buffered saline (PBS; 50 mM sodium phosphate, pH 7.4, 0,9% sodium chloride) and subsequently layered over Ficoll. Following centrifugation (30 minutes at 400×g) the supernatant was discarded and the interphase containing the lymphocytes was recovered. The lymphocytes were washed two times in PBS and were resuspended finally in cell culture medium.

A viability staining was performed by means of the trypan blue dye-exclusion method. The concentration of cells in the suspension and the percentage of viable cells were calculated. Subsequently, the cell suspension was adjusted to a concentration of $1 \times 10^7$ cells/ml. This cell suspension was transferred to tissue culture flasks: Two thirds of the cell suspension were polyclonally activated by addition of phytohemagglutinin (final concentration 5 μg.ml). One third of the cell suspension remained unstimulated.

The lymphocytes were cultivated in an incubator with a humidified atmosphere and 5% $CO_2$ for 48 to 64 hours at 37° C. Following this incubation period, cells were harvested by centrifugation, resuspended in cell culture medium and counted. Stimulated and unstimulated cells were combined in a ratio of 2:1 and adjusted to a concentration of $2 \times 10^6$ cells/ml with cell culture medium that contained, in addition, 10 units/ml of human recombinant interleukin-2.

Only those preparations of lymphocytes were employed for the screening test in which more than 70% of the stimulated lymphocytes expressed the CD 25 antigen and more than 45% of the lymphocytes expressed the CD 4 antigen.

100 μg of this lymphocyte suspension was added to each well of microtiter plates containing the test compounds serially diluted over the range 100 μM to 0.1 μM. Subsequently, the microtiter plates were cultivated for 4 days at 37° C.

Survival and proliferation of the lymphocytes grown in the presence of the compound were measured by a quantitative colorimetric assay. Viable cells cultivated in the presence of the dye MTT (3(4,5 Dimethylthiazol-2-yl)-3,5-diphenyltetrazolium) reduce this pale yellow substrate by activity of their mitochondrial dehydrogenases to a purple formazan. The amount of product which is a function of cell number and metabolic cellular activity was quantified photometrically. By this assay, potential cytotoxic and cytostatic effects of compounds towards lymphocytes were detected precisely.

Microtiter plates were centrifuged for 5 minutes at 900×g. The supernatant was discarded and the cells of each well were resuspended in 50 μl of cell culture medium containing 2 mg/ml of MTT. After four hours of incubation at 37° C. 100 μl of solvent (isopropanol with 0,04N HCl and 10% (v/v) Triton 100) was added to each well. By shaking the microtiter plates the formazan was solubilized.

Subsequently, the plates were evaluated in an ELISA photometer in the dual wavelength mode (measuring wavelength: 550 nm; reference wavelength: 690 nm).

For each well the difference in absorption (abs. 550 nm–abs. 690 nm) was calculated. These data provided the basis for further evaluation of the cytotoxicity test. The approximate $CD_{50}$-halfmaximal cytotoxic dose- of each compound was calculated.

b) HIV Suppression test

Peripheral human lymphocytes were prepared, cultivated, and harvested as above. Following the determination of the lymphocyte surface markers, unstimulated and mitogen stimulated cells were combined in a ratio of 1:2.

Under safety conditions these cells are infected with a standard preparation of HIV. The cells are sedimented by centrifugation. The supernatant was discarded and cells were resuspended in the HIV inoculum.

This inoculum is a liquid suspension of HIV-1 strain virus, pretested and adjusted to a titer that results in a synthesis of viral core protein p24 of > 100 ng/ml at day four following infection of human lymphocytes according to the protocol.

$3 \times 10^8$ lymphocytes were resuspended in 1 ml HIV inoculum and incubated at 37° C. for 60 minutes. Subsequently, the cells were washed two times with 50 ml of culture medium and resuspended in culture medium containing 10 units/ml of human recombinant interleukin-2 to yield a cell concentration of $2 \times 10^6$ cells/ml. 100 μof this cell suspension was added to each well of the microtiter plates containing the diluted solutions of the compounds. The microtiter plates were cultivated in an incubator with a humidified atmosphere and 5% $CO_2$ at 37° C.

Accordingly, a fraction of lymphocytes was mock-infected with the same virus preparation that was heat inactivated (30 minutes at 56° C.) prior to infection.

On each of the days 2,3 and 4 post infection one of the microtiter plates which had been established in triplicate was prepared for determination of viral replication. Viral RNA is determined within the cells whereas the viral core protein p24 was detected in the supernatant of the lymphocyte culture.

Accordingly, 150 μl of supernatant were removed from each well and transferred to the well of a microtiter plate containing 50 μl/well of SDS (sodium dodecylsulfate, 0.08%). These plates were stored frozen. 50 μl of stop solution (1% SDS, 20 mM sodium acetate, pH 5.0, and 200 μg/ml heparin) were added to the cells remaining in each well. The plates were stored frozen.

The concentration of p24 synthesized by the HIV infected cells was determined by means of a sandwich ELISA, while the concentration of viral RNA was quantitated by nucleic acid hybridisation, using a $^{32}P$-labelled DNA probe for the gag/pol region of the viral genome. Absolute levels of viral antigen and RNA in drug treated samples were compared with untreated, virus-infected controls and the percentage inhibition calculated.

6. Test for Feline Immunodeficiency Virus (FIV)

Drug stocks were diluted to the appropriate concentration, in medium (e.g. 10 mg/ml to 200 μg/ml). 150 μl of each drug was dispersed in triplicate, across the top row of a microtitre plate (150 μl of media for virus and cell control, vc and cc). 100 μl of medium was dispersed into all other wells. The wells were serially diluted moving down the plate, removing 50 μl from each well and transferring to the next row. 50 μl was discarded from the bottom wells.

Trypsinisation was carried out from a confluent cell monolayer of Crandell Feline Kidney cells, in 10% trypsin, followed by resuspension in media at $1 \times 10^6$ per ml, ensuring that a single cell suspension is achieved. (Media: 90% 1×RPMI, 25 mM hepes buffer; 10% Foetal calf serum; 2% Glutamine; 2% penecillin/streptomycin.)

FIV Glasgow 8 virus was diluted to 4× the required virus challenge in medium (40 $TCID_{50}$/ml). The virus infected medium was mixed with an equal volume of cell suspension, 100 μl of which was aliquoted into each well of the drug plate, except cell control. 100 μl of cell suspension at $5 \times 10^4$ per ml was added to the latter. This gives a final cell concentration of $2.5 \times 10^4$ per ml, and drug range 100-0.03 μg/ml. The plates were incubated at 37° C., 5% $CO_2$ in an air humidified incabator for 11-14 days. The cells were fixed by immersing the plates in formol; saline (10% formaldehyde; 10% 1.5M NaCl; 80% water) for 1 hour minimum. The cells were stained with 10% crystal violet for 15 minutes.

The assay was scored by looking for presence of syncitia and, virus induced cytopathic effect in the cell monolayers, under a microscope. Results are given as the minimum concentration of drug inhibiting syncitial production, minimum inhibitory concentration, MIC.

The results of the tests 1 to 6 were as follows:

| Example No. | Antiviral Activity Against Herpesviruses $IC_{50}$ (μg/ml) | | | |
|---|---|---|---|---|
| | HSV-1 | HSV-2 | VZV | CMV |
| 1 | <3 | <3 | <3 | 0.16 |
| 6 | 100 | 26 | 55 | 15 |
| 11 | 100 | >100 | >100 | 55 |
| 13 | 100 | 60 | 5 | 15 |
| 17 | 20 | 29 | <3 | 11 |

No cytotoxicity for the cell monolayers was noted with concentrations of the compounds up to 100 μg/ml in the HSV-1, HSV-2 and VZV tests. In the CMV test cytotoxicity was noted at concentrations of 10 μg/ml, for example 1.

| Antiviral Activity Against Visna Virus | |
|---|---|
| Example No. | MIC (μg/ml) |
| 1 | <0.003 |
| 3 | 10 |
| 5 | 1 |
| 6 | 0.1 |
| 8 | 0.3 |
| 10 | 100 |
| 11 | <0.03 |

At concentrations up to 100 μg/ml, the compounds were not toxic for the SCP cell monolayers used in the tests.

| | Antiviral Activity Against HIV | | |
|---|---|---|---|
| Example No. | Concn. (μM) | % Inhibition on Day 4 after infection | |
| | | Viral Antigen | Viral RNA |
| 1 | 0.1 | 93 | 93 |
| 3 | 10 | 47 | 44 |
| 8 | 10 | 37 | 62 |
| 11 | 10 | 3 | 33 |

Slight toxicity (18% inhibition) at 0.1 μM was noted for the compound of Example 1, although the $CD_{50}$ was 1 μM.

| Antiviral Activity Against FIV | |
|---|---|
| Example No. | MIC (µg/ml) |
| 1 | 0.01 |
| 3 | 10 |
| 13 | 0.10 |
| 15 | 30 |
| 17 | 0.03 |

No cytotoxicity for the cell monolayers was noted with concentrations up to 100 µg/ml for examples 1, 3 and 15. Cytotoxicity was noted at a concentration of 10 µg/ml for example 17 and at 1 µg/ml for example 13.

We claim:

1. A compound of formula (I), or a pharmaceutically acceptable salt thereof:

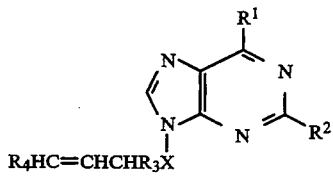

wherein

X is —$CH_2O$ or —$CH_2$;

$R_1$ is hydroxy or amino;

$R_2$ is hydrogen or amino;

$R_3$ is hydrogen, hydroxymethyl or acyloxymethyl, wherein the acyl group of said acyloxymethyl is selected from the group consisting of $C_{1-7}$ alkanoyl and benzoyl optionally substituted in the phenyl ring by one, two or three substituents selected from the group consisting of fluoro, chloro, bromo, $C_{1-4}$ alkyl and $C_{1-4}$ alkoxy, wherein the alkyl moiety of said $C_{1-4}$ alkyl and $C_{1-4}$ alkoxy substituents is selected from the group consisting of methyl, ethyl, n- and iso-propyl, n-, sec-, iso- and tert-butyl.

$R_4$ is a group of formula:

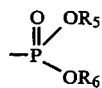

wherein $R_5$ and $R_6$ are independently selected from hydrogen, $C_{1-6}$ alkyl and phenyl optionally substituted by one, two or three substituents selected from the group consisting of fluoro, chloro, bromo, $C_{1-4}$ alkyl and $C_{1-4}$ alkoxy, wherein the alkyl moiety of said $C_{1-4}$ alkyl and $C_{1-4}$ alkoxy substituents is selected from the group consisting of methyl, ethyl, n- and so-propyl, n-, sec-, iso- and tert-butyl.

2. A compound according to claim 1 wherein $R_1$ is hydroxy and $R_2$ is amino.

3. A compound according to claim 1 wherein $R_1$ is amino and $R_2$ is hydrogen.

4. A compound according to claim 1 wherein $R_3$ is hydroxymethyl.

5. A compound according to claim 1 wherein $R_5$ and $R_6$ are both hydrogen.

6. A compound selected from the group consisting of:

(E)-9-(4-phosphonobut-3-enyloxy)guanine,
(E)-9-[4-(diisopropoxyphosphoryl)but-3-enyloxy]adenine,
(E)-9-(4-phosphonobut-3-enyloxy)adenine,
(E)-9-[4-(diisopropoxyphosphoryl)but-3-enyl]adenine,
(E)-9-(4-phosphonobut-3-enyl)adenine,
(E)-9-(4-phosphonobut-3-enyl)guanine,
(E)-2,6-diamino-9-[4-(diisopropoxyphosphoryl)but-3-enyl]purine,
(E)-2,6-diamino-9-(4-phosphonobut-3-enyl)purine,
(Z)-9-[4-(diethoxyphosphoryl)but-3-enyloxy]adenine,
(Z)-9-4-(phosphonobut-3-enyloxy)adenine,
(Z)-9-(4-(phosphonobut-3-enyloxy)guanine,
(E)-9-[4-(diisopropoxyphosphoryl)-2(hydroxymethyl)-but-3-enyloxy]guanine,
(E)-9-(2-hydroxymethyl-4-phosphonobut-3-enyloxy)-guanine,
(E)-9-[4-(diisopropoxyphosphoryl)-2(hydroxymethyl)-but-3-enyloxy]adenine,
(E)-9-(2-hydroxymethyl-4-phosphonobut-3-enyloxy)adenine,
(E)-9-[4-(diisopropoxyphosphoryl)-2-(hydroxymethyl)-but-3-enyl]adenine,
(E)-9-(2-hydroxymethyl-4-phosphonobut-3-enyl)adenine, and
(E)-9-(2-hydroxymethyl-4-phosphonobut-3-enyl)guanine.

7. A pharmaceutical composition comprising a compound according to claim 1 and a pharmaceutically acceptable carrier.

8. A method of treatment of herpesvirus infections in mammals, which comprises the administration to a mammal in need of such treatment, an effective amount of a compound according to claim 1.

* * * * *